(12) United States Patent
Gregory et al.

(10) Patent No.: US 10,751,493 B2
(45) Date of Patent: Aug. 25, 2020

(54) APPARATUS FOR PREVENTING OVER INFLATION OF THE RETENTION BALLOON IN MEDICAL CATHETERS AND AIRWAY DEVICES

(71) Applicant: ConvaTeC Technologies Inc., Las Vegas, NV (US)

(72) Inventors: Christopher Gregory, Newtown, PA (US); Yun Jin, Bedminister, NJ (US); John B. Cline, New Brunswick, NJ (US)

(73) Assignee: CONVATEC TECHNOLOGIES INC., Las Vegas, NV (US)

( * ) Notice: Subject to any disclaimer, the term of this patent is extended or adjusted under 35 U.S.C. 154(b) by 197 days.

(21) Appl. No.: 15/448,274

(22) Filed: Mar. 2, 2017

(65) Prior Publication Data

US 2017/0173310 A1    Jun. 22, 2017

Related U.S. Application Data

(63) Continuation of application No. 14/341,647, filed on Jul. 25, 2014, now Pat. No. 9,623,201, which is a
(Continued)

(51) Int. Cl.
*A61M 16/04* (2006.01)
*A61M 25/10* (2013.01)
(Continued)

(52) U.S. Cl.
CPC .......... *A61M 16/044* (2013.01); *A61F 5/445* (2013.01); *A61F 5/449* (2013.01); *A61M 3/0295* (2013.01);
(Continued)

(58) Field of Classification Search
CPC ........ A61M 5/31513; A61M 25/10184; A61M 25/10185; A61M 25/10186;
(Continued)

(56) References Cited

U.S. PATENT DOCUMENTS

| 851,530 | A | * | 4/1907 | Lamport | ................. A61M 3/00 |
| | | | | | 604/99.02 |
| 2,254,997 | A | | 9/1941 | Fisher | |

(Continued)

FOREIGN PATENT DOCUMENTS

| CN | 105407961 A | 3/2016 |
| EP | 1514572 A2 | 3/2005 |

(Continued)

OTHER PUBLICATIONS

Australia Patent Application No. 2017200016 Examination Report No. 1 dated Nov. 14, 2017.
(Continued)

*Primary Examiner* — Nilay J Shah
(74) *Attorney, Agent, or Firm* — Taft Stettinius & Hollister LLP; Ryan O. White

(57) ABSTRACT

The body has a fluid inlet port for receiving pressurized fluid and a fluid outlet port connected to the retention balloon. A first passage connects the fluid inlet port and the fluid outlet port, A second passage in the body is connected to the balloon fluid return path and is at the pressure of the retention balloon. A valve prevents fluid flow through the first passage when actuated. The valve includes a pressure-responsive member movable to a position to obstruct fluid flow in response to fluid pressure in the second passage exceeding the predetermined level. Flexible means such as a membrane defines a normally open portion of the first fluid
(Continued)

passage, which is closed by the moveable means bearing on the membrane when pressure exceeding the predetermined level actuates the valve.

30 Claims, 17 Drawing Sheets

Related U.S. Application Data continuation of application No. 13/877,890, filed as application No. PCT/US2012/065239 on Nov. 15, 2012, now Pat. No. 8,888,739.

(60) Provisional application No. 61/560,489, filed on Nov. 16, 2011.

(51) Int. Cl.
  *A61M 3/02* (2006.01)
  *A61M 16/20* (2006.01)
  *A61F 5/449* (2006.01)
  *A61F 5/445* (2006.01)

(52) U.S. Cl.
  CPC ........ *A61M 16/04* (2013.01); *A61M 16/0443* (2014.02); *A61M 16/0486* (2014.02); *A61M 16/201* (2014.02); *A61M 16/208* (2013.01); *A61M 16/209* (2014.02); *A61M 25/10182* (2013.11); *A61M 25/10183* (2013.11); *A61M 25/10185* (2013.11); *A61M 25/10187* (2013.11); *A61F 2005/4455* (2013.01); *A61M 2205/583* (2013.01)

(58) Field of Classification Search
  CPC .... A61M 25/10187; A61M 2005/3128; A61M 25/1018; A61M 25/10181; A61M 25/10; A61M 25/0075; A61M 2025/1077; A61M 25/104; A61M 16/044; A61M 2039/2473; A61M 2039/266; A61M 16/045; A61M 16/0452; F16K 17/048; F16K 1/304
  See application file for complete search history.

(56) References Cited

U.S. PATENT DOCUMENTS

| | | |
|---|---|---|
| 3,127,148 A | 3/1964 | Collar |
| 3,211,150 A | 10/1965 | Foderick |
| 3,446,245 A | 5/1969 | Clifford, Jr. |
| 3,721,726 A | 3/1973 | Schwartzman |
| 3,777,757 A | 12/1973 | Gray et al. |
| 4,116,201 A | 9/1978 | Shah |
| 4,178,938 A | 12/1979 | Au |
| 4,280,498 A | 7/1981 | Jensen |
| 4,431,019 A | 2/1984 | Kopp et al. |
| 4,541,457 A | 9/1985 | Blenkush |
| 4,629,159 A | 12/1986 | Wellenstam |
| 4,948,092 A | 8/1990 | Kasper et al. |
| 4,955,879 A | 9/1990 | Mervine |
| 5,350,364 A | 9/1994 | Stephens et al. |
| 5,454,784 A | 10/1995 | Atkinson et al. |
| 5,496,300 A | 3/1996 | Hirsch et al. |
| 5,609,195 A | 3/1997 | Stricklin et al. |
| 5,628,726 A | 5/1997 | Cotter et al. |
| 5,709,244 A | 1/1998 | Patriquin et al. |
| 5,848,997 A | 12/1998 | Erskine et al. |
| 5,957,151 A | 9/1999 | Dalcourt et al. |
| 6,045,542 A | 4/2000 | Cawood |
| 6,050,973 A * | 4/2000 | Duffy ................. A61M 25/104 137/505.13 |
| 6,146,374 A | 11/2000 | Erskine et al. |
| 6,655,656 B2 | 12/2003 | Maldavs |
| 7,261,125 B1 | 8/2007 | Lien et al. |
| 7,727,188 B2 | 6/2010 | Machado et al. |
| 8,012,132 B2 * | 9/2011 | Lum ................. A61M 5/348 604/240 |
| 8,016,816 B2 | 9/2011 | Gregory |
| 8,052,671 B2 | 11/2011 | Christensen et al. |
| 8,888,739 B2 | 11/2014 | Gregory et al. |
| 9,072,875 B2 | 7/2015 | Jin et al. |
| 9,623,201 B2 | 4/2017 | Gregory et al. |
| 9,669,205 B2 | 6/2017 | Jin et al. |
| 9,808,606 B2 | 11/2017 | Jin et al. |
| 2003/0079752 A1 | 5/2003 | Hart et al. |
| 2003/0106610 A1 | 6/2003 | Roos et al. |
| 2003/0221728 A1 | 12/2003 | Enerson |
| 2003/0229259 A1 | 12/2003 | Waksman et al. |
| 2004/0010238 A1 | 1/2004 | Manera et al. |
| 2004/0039374 A1 | 2/2004 | Tighe et al. |
| 2004/0158197 A1 | 8/2004 | Bellhouse et al. |
| 2004/0176703 A1 | 9/2004 | Christensen et al. |
| 2005/0054996 A1 | 3/2005 | Gregory |
| 2005/0082828 A1 | 4/2005 | Wicks et al. |
| 2005/0101939 A1 | 5/2005 | Mitchell |
| 2005/0124932 A1 | 6/2005 | Foster et al. |
| 2005/0256460 A1 | 11/2005 | Rome et al. |
| 2005/0273083 A1 | 12/2005 | Lebel et al. |
| 2007/0123832 A1 | 5/2007 | Cline et al. |
| 2007/0142700 A1 | 6/2007 | Fogarty et al. |
| 2007/0149922 A1 | 6/2007 | Schneider et al. |
| 2007/0155224 A1 | 7/2007 | Marot et al. |
| 2007/0215221 A1 | 9/2007 | Lien et al. |
| 2008/0009794 A1 | 1/2008 | Bagaoisan et al. |
| 2008/0103463 A1 | 5/2008 | Tsai et al. |
| 2008/0114316 A1 | 5/2008 | Christensen et al. |
| 2008/0147012 A1 | 6/2008 | Rome |
| 2008/0175719 A1 | 7/2008 | Tracey et al. |
| 2009/0029224 A1 | 1/2009 | Takahashi et al. |
| 2009/0163892 A1 | 6/2009 | McMichael et al. |
| 2010/0191192 A1 | 7/2010 | Prasad et al. |
| 2010/0217189 A1 | 8/2010 | Pepper |
| 2010/0274189 A1 | 10/2010 | Kurth et al. |
| 2011/0295236 A1 | 12/2011 | Gregory |
| 2013/0030387 A1 | 1/2013 | Williams et al. |
| 2013/0071170 A1 | 3/2013 | Menus et al. |
| 2014/0052063 A1 | 2/2014 | Gregory et al. |
| 2014/0107572 A1 | 4/2014 | Jin et al. |
| 2014/0276497 A1 | 9/2014 | Robinson et al. |
| 2015/0051542 A1 | 2/2015 | Gregory et al. |
| 2015/0059901 A1 | 3/2015 | Jin et al. |
| 2016/0339227 A1 | 11/2016 | Tsai et al. |
| 2017/0252549 A1 | 9/2017 | Jin et al. |
| 2017/0259046 A9 | 9/2017 | Jin et al. |
| 2018/0229013 A1 | 8/2018 | Tsai |

FOREIGN PATENT DOCUMENTS

| | | |
|---|---|---|
| EP | 3027266 A1 | 6/2016 |
| EP | 3297585 A1 | 3/2018 |
| JP | H09327519 A | 12/1997 |
| JP | H09512892 A | 12/1997 |
| JP | 2003502588 A | 1/2003 |
| JP | 2008117545 A | 5/2008 |
| WO | WO-8300070 A1 | 1/1983 |
| WO | WO-9530856 A1 | 11/1995 |
| WO | WO-2004045704 A2 | 6/2004 |
| WO | WO-2006/043883 | 4/2006 |
| WO | WO-2011100187 A1 | 8/2011 |
| WO | WO-2013074763 A1 | 5/2013 |
| WO | WO-2013109293 A1 | 7/2013 |
| WO | WO-2015017646 A1 | 2/2015 |
| WO | WO-2016187350 A1 | 11/2016 |
| WO | WO-2017075226 A1 | 5/2017 |

OTHER PUBLICATIONS

Japanese Patent Application No. 2014-542455 Office Action dated Nov. 14, 2017.
PCT/US2016/033147 International Preliminary Report on Patentability dated Nov. 30, 2017.
U.S. Appl. No. 15/495,712 Office Action dated Jan. 5, 2018.

(56) References Cited

OTHER PUBLICATIONS

Australian Patent Application No. 2012340411 Examiners First Report dated Jul. 14, 2016.
Chinese Patent Application No. 201280067212.0 Second Office Action dated Jul. 12, 2016.
Chinese Patent Application No. 201280067212.0 Third Office Action dated Feb. 27, 2017 (No translation provided to date).
European Patent Application No. 12849279.0 Communication dated Aug. 18, 2016.
European Patent Application No. 12849279.0 Communication dated Mar. 23, 2016.
Japanese Patent Application No. 2014-542455 Office Action dated Dec. 6, 2016.
Mexican Patent Application No. MX/a/2014/005934 Office Action dated Jul. 14, 2016.
New Zealand Patent Application No. 727366 First Examiners Report dated Jan. 17, 2017.
PCT Patent Application No. PCTUS2014/049115 International Preliminary Report dated Feb. 11, 2016.
PCT/US2012/025420 International Preliminary Report on Patentability dated Aug. 21, 2013.
PCT/US2012/025420 International Search Report and Written Opinion dated Jun. 6, 2012.
PCT/US2012/065239 International Preliminary Report on Patentability dated May 20, 2014.
PCT/US2012/065239 International Search Report completed Mar. 8, 2013.
PCT/US2012/065239 Written Opinion completed Mar. 8, 2013.
PCT/US2014/049115 International Preliminary Report on Patentability dated Feb. 11, 2016.
PCT/US2014/049115 International Search Report completed Oct. 28, 2014.
PCT/US2014/049115 Written Opinion completed Oct. 28, 2014.
PCT/US2016/033147 International Search Report and Written Opinion dated Aug. 16, 2016.
ROC (Taiwan) Patent Application No. 101142959 Office Action dated Mar. 21, 2016.
Russian Patent Application No. 2014124144 Office Action dated Nov. 14, 2016.
Taiwan Patent Application No. 105113600 Office Action dated Jan. 16, 2017.
U.S. Appl. No. 13/877,890 Office Action dated Mar. 27, 2014.
U.S. Appl. No. 14/000,384 Office Action dated Sep. 11, 2014.
U.S. Appl. No. 14/341,647 Office Action dated May 5, 2016.
U.S. Appl. No. 14/449,035 Office Action dated Feb. 12, 2016.
U.S. Appl. No. 14/449,035 Office Action dated Sep. 14, 2016.
U.S. Appl. No. 14/745,312 Office Action dated Feb. 17, 2016.
European Patent Application No. 14832568.1 Supplementary European Search Report dated Feb. 15, 2017.
U.S. Appl. No. 15/495,712 Restriction Requirement dated Oct. 6, 2017.
Japanese Patent Application No. 2016-531895 Office Action dated Jun. 11, 2019.
PCT/US2016/059132 International Preliminary Report on Patentability dated May 1, 2018.
PCT/US2016/059132 International Search Report and Written Opinion dated Jan. 6, 2017.
U.S. Appl. No. 15/158,426 Office Action dated Aug. 27, 2018.
U.S. Appl. No. 15/158,426 Office Action dated Jun. 25, 2019.
U.S. Appl. No. 15/158,426 Office Action dated Mar. 4, 2019.
U.S. Appl. No. 15/448,274 Office Action dated Jul. 17, 2019.
U.S. Appl. No. 15/495,712 Advisory Action dated Dec. 13, 2018.
U.S. Appl. No. 15/495,712 Office Action dated Jan. 24, 2019.
U.S. Appl. No. 15/495,712 Office Action dated Sep. 5, 2018.

* cited by examiner

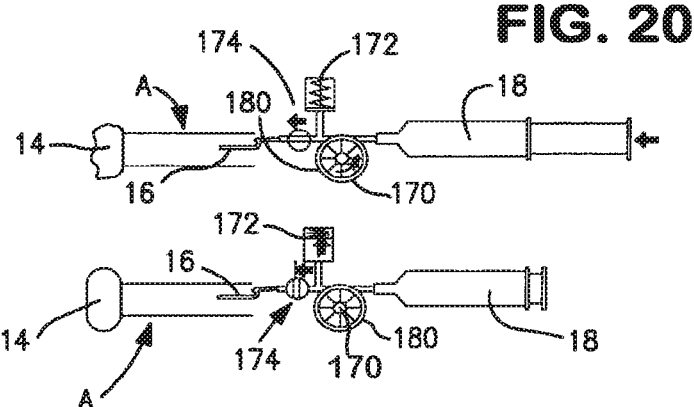
FIG. 20
FIG. 21
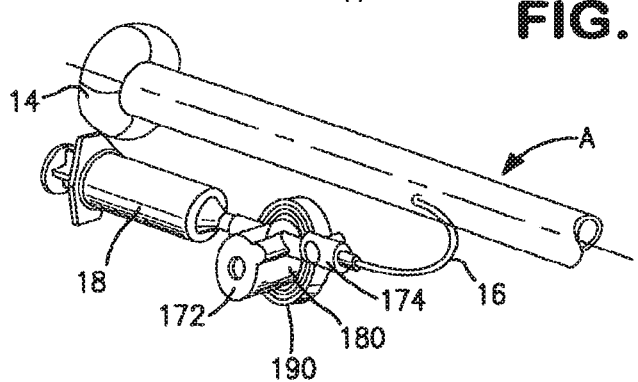
FIG. 22
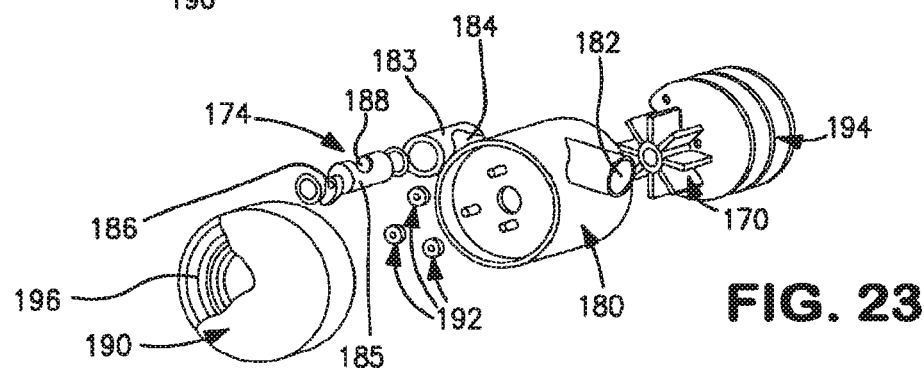
FIG. 23
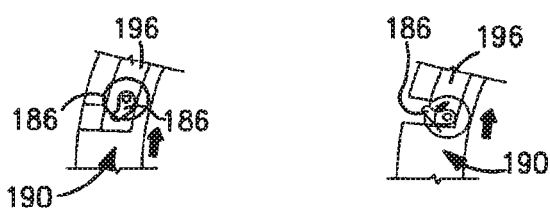
FIG. 24
FIG. 25

APPARATUS FOR PREVENTING OVER INFLATION OF THE RETENTION BALLOON IN MEDICAL CATHETERS AND AIRWAY DEVICES

CROSS-REFERENCE TO RELATED APPLICATIONS

This application is a continuation application of U.S. patent application Ser. No. 14/341,647, filed on Jul. 25, 2014, now U.S. Pat. No. 9,623,201, which issued on Apr. 18, 2017, which is a continuation of U.S. patent application Ser. No. 13/877,890, filed on May 30, 2013, now U.S. Pat. No. 8,888,739, which issued on Nov. 18, 2014, which is a U.S. National Phase of PCT/US12/65239, filed on Nov. 15, 2012, which claims the benefit of U.S. Provisional Patent Application No. 61/560,489, filed Nov. 16, 2011, each of which are entirely incorporated herein by reference.

BACKGROUND OF THE INVENTION

Field of the Invention

The present invention relates to medical devices with inflatable retention balloons and more particularly to an apparatus for preventing over inflation of the catheter retention balloons in a fecal management system or an endotracheal tube.

Description of Prior Art Including Information

Fecal management systems, such as the one disclosed in U.S. Pat. No. 8,016,816, issued Sep. 13, 2011 to Christopher C. Gregory, which patent is incorporated herein by reference, are known in the art. The system disclosed in the Gregory patent is a medical appliance formed of an elongated flexible tubular element or catheter having a distal end designed to be introduced into a body cavity, such as the rectum through the anal sphincter. The proximal end of catheter is connected to a receptacle for the collection of fecal waste.

Affixed to the exterior surface of the distal end of the catheter is an inflatable balloon which serves to retain the distal end of the catheter within the body cavity. The balloon is inflated to a suitable diameter with fluid, such as air, water or saline, through a fluid supply tube or lumen, after it is inserted into the body cavity. The supply lumen is connected to a source of pressurized inflation fluid, such as a syringe. The syringe is also used to withdraw the inflation fluid through the supply lumen, to deflate the balloon.

A second lumen may be provided to deliver irrigation fluid to the body cavity. One end of irrigation lumen extends through a port in the distal end of the catheter. The other end is connected to a source of irrigation fluid.

The distal end of the catheter and the retention balloon are both made entirely of soft, compliant material, for example, silicone, so as not to injure any body tissue.

The retention balloon surrounds the distal end of the catheter and preferably has a toroidal shape when fully inflated. The wall of the balloon may be fabricated in its fully inflated shape of material that allows the balloon to be inflated to its final shape.

Fecal management systems using an inflated retention balloon must be used carefully because they can create too much pressure on the rectal tissue if the retention balloon is over inflated. That pressure is a result of the balloon being filled with a volume of fluid greater the space available in the body cavity. Accordingly, all fecal management systems have an indicated maximum volume for the retention balloon that each manufacturer has established as safe. However, this maximum balloon volume can be exceeded by over inflating the balloon, resulting in damage to the soft tissue surrounding the balloon.

Similarly, endotracheal tubes have affixed to the exterior surface of the distal end of the catheter an inflatable balloon which serves to retain the distal end of the catheter within the body cavity and create an air seal to the trachea. The balloon is inflated to a suitable diameter with fluid, such as air, through a fluid supply tube or lumen, after it is inserted into the trachea. The supply lumen is connected to a source of pressurized inflation fluid, such as a syringe. The syringe is also used to withdraw the inflation fluid through the supply lumen, to deflate the balloon. In an endotracheal tube, the retention balloon surrounds the distal end of the catheter and preferably has a toroidal shape when fully inflated. The wall of the balloon may be fabricated in its fully inflated shape of material that allows the balloon to be inflated to its final shape.

Endotracheal systems using an inflated retention balloon must be used carefully because they can create too much pressure on the mucosal tissue in the trachea if the retention balloon is over inflated. That pressure is a result of the balloon being filled with a volume of fluid greater the space available in the trachea. Accordingly, all endotracheal tubes have an indicated maximum volume for the retention balloon that each manufacturer has established as safe or pressure monitoring mechanisms. However, this maximum balloon volume or pressure can be exceeded by over inflating the balloon, resulting in damage to the soft tissue surrounding the balloon.

Although one commercially available fecal management system (Flexi-Seal® SIGNAL™ FMS) can be obtained with an indicator that tells the clinician when the balloon is properly filled, there continue to be cases where clinicians have initially over inflated the retention balloon, or have added more fluid to the balloon after the catheter has been in use, resulting in a potentially hazardous situation.

Another disclosed system employs a catheter with a pressure relief valve. However, that approach has not proved to be practical because in use there are frequently brief periods of muscle contraction in the rectum that result in high pressure in the balloon. In the trachea there are periods of high pressure during the respiratory cycle. If the inflation fluid were allowed to escape under those high pressure conditions, the retention of the device would be compromised and the catheter expelled or the seal lost. Accordingly, neither of these approaches has proved successful.

Another possible approach to the over inflation problem would be to electronically measure the amount of inflation fluid provided to the balloon. Accurate measurement of the volume of a flowing fluid through a tube requires the measurement of the flow rate of the fluid and of the time during which the fluid is flowing. Those values can then be multiplied to calculate the total volume of fluid that has passed through the tube. This is typically done through real time electronic measurement of the flow rate which utilizes the cooling ability of the fluid across a heated probe, and a microprocessor completing the calculations.

For prevention of the delivery of too much fluid, the result of this calculation then has to control a valve or actuate an alarm to prevent additional fluid from being added to the balloon. Clearly, devices using this method of calculating the amount of fluid used to inflate the balloon are complex and costly. Moreover, they have difficulty in taking into account the fact that the fluid can and needs to be able to be withdrawn from the balloon, as well as provided to the balloon, because they cannot easily differentiate between the flow directions. Simpler and less expensive options are desirable, and are provided by the present invention.

The present invention relates to apparatus designed for use as part of a fecal management system or endotracheal tube of the type including a catheter with an inflatable retention balloon. The apparatus is utilized as part of the fluid inflation system and several different device configurations and modes of operation are disclosed which prevent over inflation of the retention balloon by limiting the flow of inflation fluid to the catheter balloon to a specific volume or pressure.

BRIEF SUMMARY OF THE INVENTION

Two different basic approaches are proposed to prevent over inflation of the catheter retention balloon. One approach involves monitoring the fluid pressure in the balloon as it is filled from a source of pressurized fluid and preventing additional fluid from entering the balloon after a predetermined pressure level in the balloon is reached. The other approach involves monitoring the volume of fluid provided to the balloon and preventing additional fluid from entering the balloon after a predetermined volume of fluid has been provided to the balloon.

In a first preferred embodiment of the present invention using the pressure monitoring approach, the apparatus is incorporated in the fill port of the catheter to prevent over inflation of the catheter retention balloon by monitoring the pressure in the balloon. It utilizes the pressure in a fluid connection to the balloon, which connection includes a return lumen separate from the supply lumen, to close a valve in the fill line to stop the flow of fluid into the balloon when the pressure in the balloon exceeds a pre-determined level.

Fluid under pressure is supplied to the inlet port of the apparatus body. A valve in the pressure cap of the body is secured to the base of the body to create a path to carry fluid from the inlet port of the body to the outlet port of the body, the latter of which is connected to the supply lumen of the balloon. The valve utilizes a pressure responsive deformable member which moves to a position to press on a flexible membrane to seal the fluid flow path to prevent over filling of the retention balloon.

The deformable member has an area significantly larger than the flow area under the membrane to permit the lower pressure in the balloon to stop the higher pressure fluid flow. Preferably, the moveable member which presses on the membrane is a dome or other structure which deforms suddenly when a predetermined pressure level is reached. Most preferably, the structure incorporates or is made as a snap dome which is bi-stable such that it can move between two positions, one of which is remote from the membrane, and thus does not block the fill line, and the other of which bears on the membrane to block the fluid flow.

The apparatus body is built out of two molded parts that do not have fluid flow passing between them, except through the catheter balloon. An integrated indicator that signals prior to or simultaneous with the valve closing off may be provided.

A check valve is used to control the flow path to permit removal of fluid from the balloon through the supply lumen to deflate the balloon. The check valve element may be a ball, flap, duck bill, or umbrella valve, as described in detail below. The check valve element may also consist of two or more separate flow channels employed in conjunction with the flexible membrane, as disclosed in one version of the preferred embodiments.

Preferably, the deformable structures of the apparatus are molded silicone rubber, polyurethane or other thermoplastic elastomer.

More specifically, apparatus for preventing over inflation of the catheter retention balloon of a fecal management system is provided. The fecal management system is of the type designed for use with a source of pressurized fluid having an associated connector. The retention balloon has a fluid port to the supply line and a fluid port to the return line. The apparatus body has a fluid inlet port for receiving the connector associated with the pressurized fluid source and a fluid outlet port connected to the fluid supply line of the balloon. The body has a first flow passage which connects the fluid inlet port and the fluid outlet port to permit fluid to be provided to the retention balloon during inflation and removed from the retention balloon during deflation. A second chamber in the body is connected to the fluid return of the balloon by a return lumen such that it is at or very close to the same fluid pressure as the retention balloon. The chamber maintains a pressure very close to the balloon pressure since there is very little flow in the return line resulting in minimal pressure drop through the return line. Means are provided for preventing fluid flow through the first passage of the body when the fluid pressure in the second chamber of the body exceeds a pre-determined pressure level.

The fluid flow preventing means may take a variety of forms. In one preferred embodiment, moveable means are provided for dividing the second or return chamber into a first portion connected to the fluid return port of the balloon and a second portion. The moveable means is movable between a first position, wherein fluid flow through the first passage is not obstructed, and a second position, wherein fluid flow through the first passage is prevented. The moveable means is moved from its first position to its second position in response to fluid pressure in the first portion of the second chamber exceeding the predetermined pressure level.

Flexible means are located in the second portion of the second chamber. The flexible means defines a normally open portion of the first fluid passage. That portion of the first fluid passage is closed by the moveable means bearing on the flexible means, when the moveable means is in its second position.

The first passage includes a first section connected to the fluid inlet port of the body and a second section connected to the fluid outlet port of the body. The normally open portion of the first fluid passage at least partially defines a connection between the first section of the first passage and the second section of the first passage.

The moveable means is situated either in the first position or in the second position. Means are associated with the moveable means for urging the moveable means toward its first position.

In one version of this preferred embodiment, the moveable means takes the form of a dome-shaped member. The dome-shaped member is formed of rigid or semi-rigid material.

The flexible means may take the form of a membrane. Means situated in the second portion of the second passage are provided for concentrating the effect of the moveable means on the flexible means.

Means for venting the second portion of the second chamber are provided to allow air that would otherwise be trapped in the second portion of the second chamber under the moveable means to escape, such that the moveable means can move from its first position to its second position.

A one-way check valve is situated between the sections of the first passage. That valve prevents fluid flow from the first section of the first passage to the second section of the first passage, except through the connection defined by the flexible means, when the pressurized fluid source is connected to the fluid inlet port to inflate the retention balloon.

Pressure indicating means may be associated with the first portion of said second chamber.

In another version of the first preferred embodiment, the sections of the first passage are each divided into first and second branches. The connection between the sections of the first passage is a connection between the first branch of the first section and the first branch of the second section. A structure, including a surface situated over the branches, is provided to support the flexible means. The surface has ports aligned with the first and second branches of the first section and with the first and second branches of the second section, respectively. A retainer is provided for holding the flexible means in place on the structure surface. The retainer has a first opening situated over the ports aligned with the first branch of the first section and the first branch of the second section. The moveable means causes the membrane to close the connection between the port aligned with the first branch of the first section and the port aligned with the first branch of the second section, when the moveable means is in the second position.

The flexible means has a hole situated over the port aligned with the second branch of the second section. The retainer also includes a second opening situated over the hole in the flexible means.

The multiple branch structure eliminates the necessity of a discrete fill check valve between the sections of the first passage. It allows the moveable means and flexible means to prevent fluid flow through the first passage when the given pressure level is exceeded and at the same time allows fluid to be withdrawn from the balloon to deflate the balloon when the moveable means is in its first position.

In the second preferred embodiment of the present invention, the fill volume is set during balloon inflation and fluid resulting in excess pressure is allowed to escape, but only during the inflation process. This prevents over inflation of the retention balloon by limiting the amount of fluid retained in the balloon according to the pressure in the balloon. During the inflation process, fluid in the balloon has access to a pressure relief valve but the balloon fluid is isolated from the relief valve once the inflation process is ended. Thus, surges in pressure during normal use do not deflate the balloon and the device remains viable.

The preferred configuration is to not make the connection between the pressure relief valve and the balloon through the supply lumen as the pressure drop through the supply lumen is very large during inflation. This large pressure drop would easily result in the fluid flowing out of the pressure relief valve, rather than to the retention balloon.

In one version, the insertion into the fluid inlet port of the body of the connector associated with the source of pressurized fluid, typically a syringe, opens two valves. The first valve is situated in the fluid passage between the syringe and the retention balloon. That valve prevents the fluid from spilling out of the balloon once the syringe is removed. The second valve is situated in a return passage from the balloon, in series with the return line and the pressure relief valve.

The second valve is held open only when the syringe is received in the port. Holding the second valve open enables the pressure relief valve to prevent overpressure in the balloon. The dual syringe actuated valves are connected mechanically but the fluid path from one to the other flows through the balloon when open. When the second valve is closed, the flow of fluid to the pressure relief valve is stopped. The pressure then equalizes throughout the system and flow between the two valves becomes irrelevant.

The mechanical opening of the second valve can be done by an external element of the syringe pressing against a mechanical element. This introduces some probability of user interference with the mechanism, so shielding of these elements can be used to prevent user interference with the mechanism.

In a specific configuration, the mechanism that moves when the syringe forces the first valve open extends on to act as the driving element for the second valve. In a syringe actuated valve, during connection the syringe tip presses on the stem of the valve pushing the stem's sealing surface away from the valve seat thus opening the valve and allowing fluid to pass through. The valve stem has a return and sealing force from a spring located or integrated behind the stem.

There is an extension to the stem that extends through the core of the spring, and passes through an opening a wall in the body with a seal into another chamber. In the second chamber, the extended stem tip interfaces with a second seal. When the syringe tip pushes the stem in, the motion continues through to the second chamber and the extended tip lifts a second seal off of its seat. Opening this second valve opens the path to the pressure relief valve.

The seal between the two chambers is only relevant when the syringe is connected. To ensure that seal, the stem has a conforming feature that seals the opening between the chambers as the stem moves to its open position. Disconnecting the syringe allows the stem to return to its normal position, sealing both valves, and isolating the pressure relieve valve from the return flow path.

In another version, the mechanism that moves when the syringe forces the first valve open extends on to act as the driving element for the second valve which is in the form of a "duckbill" valve. In a syringe actuated valve, during connection the syringe tip presses on the stem of the valve pushing the stem's sealing surface away from the valve seat thus opening the valve and allowing fluid to pass through. The valve stem has a return and sealing force from a spring located or integrated behind the stem.

In this version, there is an extension to the stem that extends through the core of the spring, passes through a wall with a seal into another chamber. In the second chamber, the extended stem tip interfaces with the side of a duckbill valve. When the syringe tip pushes the stem in, the motion continues through to the second chamber and the extended tip deforms the duckbill valve, opening it. Opening this second valve opens the fluid flow path to the pressure relief valve. The seal between the two chambers is only relevant when the syringe is connected. Disconnecting the syringe allows the stem to return to its normal position, sealing both valves and isolating the pressure relieve valve from the return flow path.

In another version, if the pressure in the return line exceeds a predetermined limit, it can force a path through a pressure relief umbrella valve but only if it can then pass on through a flow valve in the fluid escape path. The flow valve, which takes the form of a "duckbill" valve, is opened only when the fluid supply system (syringe) is attached. Connecting the syringe depresses a lever that drives a pin through the duckbill, forcing it open to allow fluid flow out of the system. The duckbill valve could also be replaced by a spring actuated flow valve that prevents flow out of the system unless the pin pushes the valve open. The flow valve and the pressure relief valve can be interchanged in order on the return line without detrimental effect to the functioning of the system.

In another version, the pressure in the return line is used to close a valve on the fill port preventing the overfilling of the balloon. The flow in the return line to the second chamber pressurizes the area under the dome. Once the pressure is sufficient to overcome the moving membrane return forces and the dome return force, the stem is pulled forcing it against the second valve seat stopping flow. The high pressure in the first chamber would force the stem into the closed position if it were not for the counterbalancing effect of the two moving membrane seals. The only forces acting on the stem is the pull from the membrane dome and the spring force of the membrane seals.

In another embodiment, the pressure in the return line is used to inflate a return balloon that actuates a valve system to stop flow into the retention balloon. The return balloon expands under pressure and pulls the stem closing the valve and stopping flow to the retention balloon. Further fluid supplied through the Luer valve only forces the second valve more tightly closed. Pulling fluid out of the supply passage will create enough vacuum to overcome the sealing of the second valve, opening it and allowing the fluid to be extracted from the catheter.

The return balloon preferably has a toroidal or annular shape with the stem passing through the center opening. Other configurations of the return balloon are just as viable such as a nearly closed "C" shape to allow easy assembly.

In another version of this embodiment, the pressure in the return line is used to inflate a return balloon that crimps a piece of tubing in the fluid supply path. The return fluid pressure expands the return balloon. The expanding return balloon presses a pressure plate against the bend of the supply tubing crimping it and stopping flow. The large area of the return balloon and the small area of the supply tubing allow the low return pressure to block the high pressure supply tubing. A separate one-way valve connecting the fluid input side of the supply tubing with the return line allows fluid to be withdrawn from the system reducing the pressure in the return balloon and thus reopening the supply tubing.

In a further embodiment, the pressure in the return line is used to deflect a flexible element. The flexible element forces a valve to close against a port in the retention balloon inflation line. The flexible element can be connected to the valve via a push rod. The push rod may or may not be fixed to either the flexible element or the valve. The valve may be a poppet valve with a stem, where the stem includes sealing means that prevents leakage of fluid out of the system.

Alternatively, the valve may be sealed by means of a flexible diaphragm, a balloon, or any flexible element that deforms with sufficient force when pressurized to apply sealing force to the valve. The flexible element can bear against an over-center spring that is displaced when a predetermined force is applied to it. The spring allows the valve to remain open until it is forced closed under sufficient balloon pressure.

The spring may be a disc, a dome, a leaf spring, or any spring configuration that can be significantly displaced when a predetermined force is applied. The spring may be configured to return to its rest position once applied force drops below the threshold level. Or it may be a bi-stable spring that requires manual resetting. This configuration allows the valve to stay fully open regardless of fill pressure or fill flow rate, and causes it to close rapidly when the retention balloon reaches the desired pressure, regardless of fill pressure or flow rate.

Turning now to volume monitoring approaches, rather than involve electronics, in one preferred embodiment a paddle wheel flow indicator is used to drive a mechanism that controls a valve. All the flow in and out of the balloon is forced to pass through a paddle wheel or similar component. The fluid flowing through forces the wheel to turn. If the fluid is incompressible and cannot leak around the wheel, the amount of rotation will be an exact indication of the amount of fluid that has passed through the device. The motion of the wheel is then used to drive a valve stem that shuts off the flow once a predetermined total volume is achieved. There is an accumulator of flexible construction between the wheel and the valve so that enough fluid can be withdrawn (from the accumulator) with the valve closed so that the wheel can open the valve for fluid withdrawal.

In another preferred embodiment, the retention balloon is supplied in a closed form with the maximum allowable amount of inflation fluid already in the system. The inflation system has a reservoir that is permanently connected to the supply line. Once the retention balloon is inserted, the fluid is transferred from the external reservoir to the internal retention balloon and an interconnecting valve is closed. For removal, the fluid is transferred back from the retention balloon to the external reservoir. As the device needs to be re-inflatable, this process can be repeated.

A number of structures can be used to act as the reservoir. The reservoir may be a collapsible structure which the clinician squeezes or applies pressure to in order to force the fluid into the retention balloon. The collapsible reservoir is either spring loaded or of a spring back structure so that it can draw the fluid out for removal. This configuration can also be combined with a pressure responsive indicator allowing customization of the fill volume with less than the total fluid in the reservoir.

In an alternate version, the reservoir is similar to a syringe with a bellows-like portion. The clinician applies force on the bellows-like portion to push the fluid into the retention balloon or remove fluid from the retention balloon. The syringe is permanently attached so a valve or clamp is used to hold the fluid in the reservoir or balloon.

The present invention may also be used with other medical catheters to limit the fill volume to a specific volume or pressure wherein the medical catheter has a fluid filled balloon requiring prevention from overfill.

BRIEF DESCRIPTION OF THE SEVERAL VIEWS OF DRAWINGS

To these and to such other objects that may hereinafter appear, the present invention relates to apparatus for preventing over inflation of the catheter retention balloon in a fecal management system or in an endotracheal tube as described in detail in the following specification, and recited in the annexed claims, taken together with the accompanying drawings, in which like numerals refer to like parts and in which:

FIG. 20 is an elevation view of the sixth preferred embodiment of the present invention, showing the apparatus during inflation;

FIG. 21 is an elevation view of the sixth preferred embodiment of the present invention, showing the apparatus after inflation;

FIG. 22 is a perspective view of the sixth preferred embodiment of the present invention;

FIG. 23 is an exploded view of the sixth preferred embodiment of the present invention;

FIG. 24 is a detailed view showing the cam follower member of the sixth preferred embodiment of the present invention in the closed position;

FIG. 25 is a detailed view showing the cam follower member of the sixth preferred embodiment of the present invention in the open position;

DETAILED DESCRIPTION OF THE INVENTION

Figure 1:
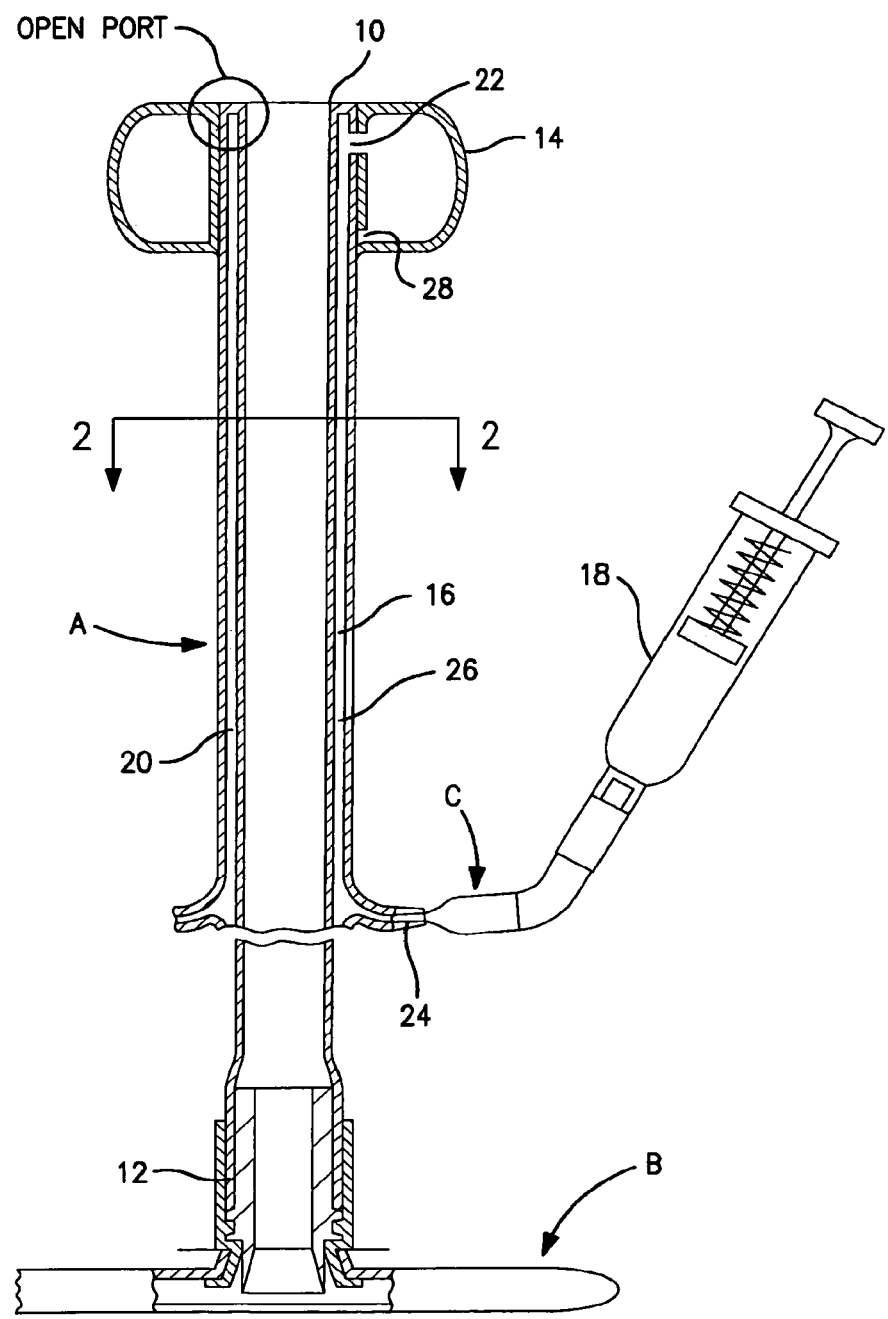
FIG. 1 is an elevation view of a typical fecal management system with the over Inflation preventing apparatus of the present invention.

The present invention is designed for use as part of a tubular medical device which utilizes an inflatable retention balloon. The basic components of one such system are illustrated in FIG. 1. The system is a medical appliance formed of an elongated flexible tubular element or catheter, generally designated A, having a distal end 10 which is introduced into a body cavity, such as the rectum through the anal sphincter or the trachea through the mouth. The proximal end 12 of catheter A is connected to a receptacle, generally designated B, for the collection of fecal waste or a respiratory management system for an endotracheal tube. Affixed to the exterior surface of the distal end 10 of catheter A is a low-pressure inflatable retention balloon 14, shown in its inflated state.

Balloon 14 is inflated to a suitable diameter with fluid, such as air, water or saline, through a fluid supply lumen 16 after the balloon is inserted into the body cavity such that the distal end of the catheter is retained in place within the body cavity. One end of supply lumen 16 is connected to a source of pressurized inflation fluid, shown in the figure as a syringe 18. The syringe is also used to withdraw the inflation fluid, to deflate the balloon, through supply lumen 16. Other type sources of fluid may be used instead of a syringe, such as a collapsible reservoir or a mechanical pump.

An irrigation lumen 20 may be provided to deliver irrigation fluid to the body cavity. One end of irrigation lumen 20 extends through a port at the distal end 10 of catheter A. The other end is connected to a source of irrigation fluid (not shown).

The distal end 10 of catheter A and balloon 14 are both made entirely of soft, compliant material, for example, silicone, so as not to injure any body tissue.

Balloon 14 surrounds the distal end 10 of catheter A and preferably has a toroidal shape when fully inflated. Supply lumen 16 is connected to balloon 14 through a fluid inlet 24 proximate the distal end 10 of the catheter to permit the inflation fluid to be introduced into balloon 14 to inflate the balloon and to be removed from the balloon to deflate the balloon.

The apparatus of the present invention, generally designated C, is connected between the source of pressurized inflation fluid, in this case syringe 18, and the other end 24 of the supply lumen. The pressure of the fluid within balloon 14 is limited to a predetermined pressure level by apparatus C, such that the balloon cannot apply a pressure beyond a predetermined level on the surrounding tissue which will injure the patient. As the balloon is inflated by the inflation fluid, apparatus C avoids over inflation of the balloon by preventing additional fluid from being provided to the balloon when the fluid pressure of the balloon reaches a preset level.

Figure 2:
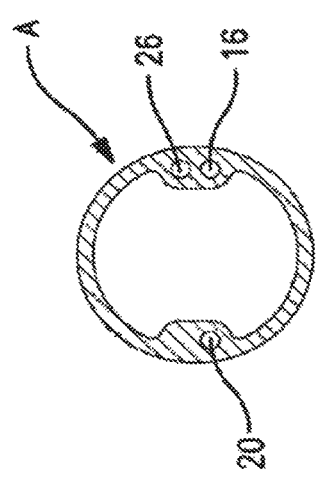
FIG. 2 is a cross-sectional view of the catheter of the fecal management system of FIG. 1.

In the preferred embodiments of the present invention which use the pressure monitoring approach, apparatus C is connected to balloon 14 by a second, return lumen 26 through a fluid return port 28 in the balloon such that apparatus C can monitor the pressure in the balloon. As best seen in FIG. 2, which is a cross-section of catheter A, supply lumen 16 and return lumen 26 extend between apparatus C and the balloon, separately, in side-by-side relation, preferably within the outside profile of the catheter.

In some of the preferred embodiments of the invention, the pressure in the return line is used to deflect a flexible element which functions as a valve. The flexible element forces a seal which closes to block the balloon inflation line when the pressure in return lumen 26, and thus in balloon 14, exceeds a pre-determined level. The valve may be sealed by means of a membrane, a diaphragm, a balloon, or any flexible element that deforms with sufficient force when pressurized to apply sealing force to the valve.

The flexible element can act with an over-center spring member that is displaced when a predetermined force is applied to it. The pressure responsive spring member allows the valve to remain open until it is forced closed under sufficient balloon pressure. The spring member may take the form of a disc, a dome, a leaf spring, or any spring configuration that can be significantly displaced when a predetermined force is applied.

The spring member may be configured to return to its rest position once the applied force drops below the threshold level. Or it may take the form of a bi-stable member that requires manual resetting. This configuration allows the valve to stay fully open regardless of fill pressure or fill flow rate, and causes it to close rapidly when the balloon reaches the desired pressure, regardless of fill pressure or flow rate. An alternate flow path may be supplied with a one-way check valve to allow fluid to be removed from the system to deflate the retention balloon when necessary.

Figure 3:
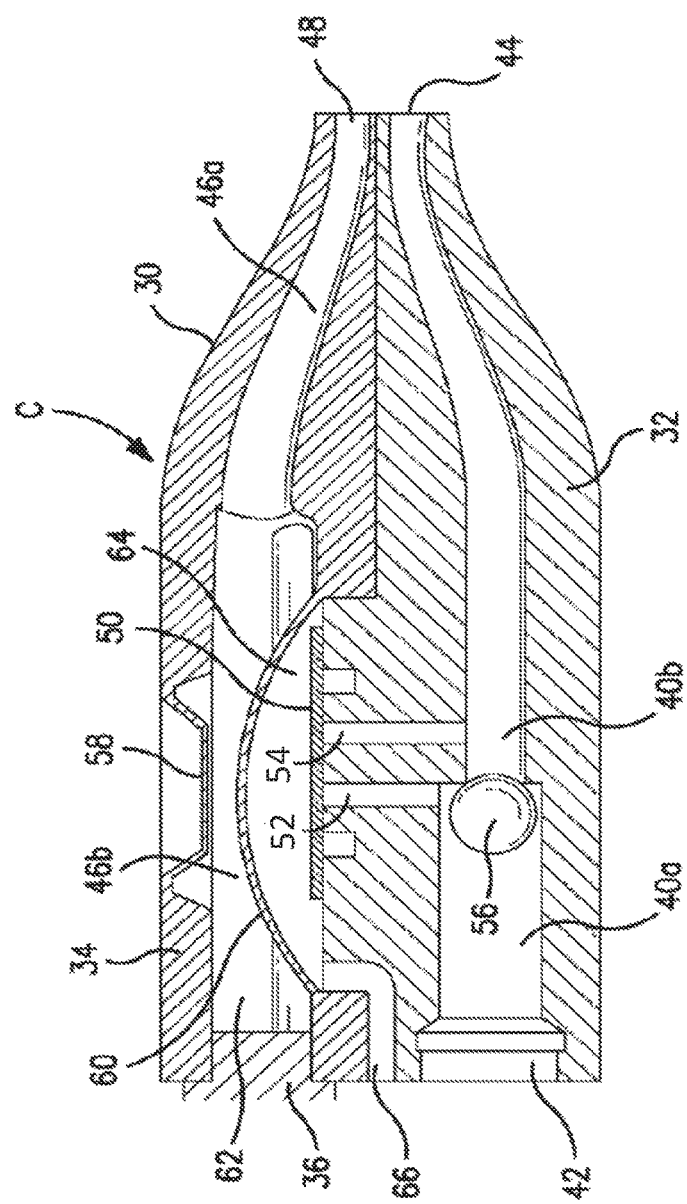
FIG. 3 is a cross-sectional view of a first version of the first preferred embodiment of the present invention.

FIG. 3 is a cross-sectional view of a configuration of a first version of a first preferred embodiment of the present invention. The apparatus takes the form of a body 30 which includes a base 32 and a pressure cap 34. Body 30 is connected to both supply lumen 16 and return lumen 26 of a balloon catheter.

Base 32 includes a first passage which includes sections 40a and 40b. First passage extends the entire length of body 30, between a fluid inlet port 42, which is designed to accept a connector associated with the source of pressurized fluid, and a fluid outlet port 44, which is connected to end 24 of supply lumen 16. It provides a fluid connection between the source of pressurized inflation fluid and fluid inlet 22 of the balloon. A valve (not shown in this figure) is pressed into the socket which forms inlet port 42 to allow coupling of the body to a fluid supply device such as syringe 18.

Pressure cap 34 has a second chamber which includes sections 46a and 46b. Passage section 46a is connected to a return port 48 which in turn is connected to return lumen 26, and hence to balloon 14 through fluid return port 28. Thus, the fluid pressure in section 46a is essentially the same as the pressure in the balloon. The flexible valve element is situated under chamber section 46b, as explained below. A plug 36 is used to seal an opening in pressure cap 34 at the end of section 46a which is required to withdraw a mold core.

In this preferred embodiment, the flexible element takes the form of a flexible valve membrane 50 which is glued to the top surface of base 32 such that when pressure cap 30 is fitted over base 32, membrane 50 is situated under section 46b. Within base 32 are spaced, parallel channels 52 and 54 extending from passage sections 40a and 40b, respectively. Channels 52 and 54 terminate at spaced locations under membrane 50. Accordingly, a fluid connection between passage section 40a and passage section 40b through channel 52, under membrane 50, and through channel 54, is formed.

In normal filling, fluid flows into passage section 40a from the pressurized fluid source through the inserted valve (not shown in this figure) in inlet port 42. The pressure forces a fill check valve ball 56 within passage section 40a against the port between passage sections 40a and 40b, closing that port. That forces fluid to flow up through channel 52, under membrane 50 over and back down channel 54 to the passage section 40b. The fluid then flows out port 44 and through supply lumen 16 to the catheter balloon.

Return pressure comes back from the balloon to apparatus C through return lumen 26. The return lumen connects into return port 48 of the body such that chamber 46a receives the pressure from balloon 14. The pressure builds in the chamber section 46b until the critical level for an indicator pop dome 58 situated on the top surface of the pressure cap is reached. At that point, dome 58 expands outward, indicating that the appropriate pressure has been reached.

Situated within chamber section 46b is a domed-shaped pressure-responsive valve member 60. Member 60 is located over membrane 50 and divides chamber section 46b into two portions 62 and 64. Portion 62 of passage section 46b is connected to the return lumen through chamber section 46a and port 48.

As inflation of the retention balloon continues, the pressure in portion 62 of chamber section 46b increases until the pressure-responsive valve member 60 collapses, pressing membrane 50 down against the top surface of base 32, at a point between the ends of channels 52 and 54 to close the fluid connection between channels 52 and 54, stopping fluid flow the balloon. To allow member 60 to collapse, the air under member 60 must be allowed to escape. This is done through a pressure relief channel 66 which vents portion 64 of chamber section 46b to the environment.

To empty the balloon, fluid is drawn from inlet port 42. The reduction in pressure draws the fill check valve ball 56 away from the port between passage sections 40a and 40b, allowing fluid to flow out directly from passage section 40b to passage section 40a around ball 56. This is also creates suction which will collapse the membrane against the top surface of base 32.

The pressure-responsive member 60 can be made as or joined with a bi-stable structure, such as snap dome or any of the other embodiments described herein. Preferably, the pressure-responsive member is constructed to enable a definitive snap shut off of flow, making the difference between open and closed states of the valve more distinct and consistent as the flow path will be either totally open or totally closed when the target pressure is reached, regardless of how quickly the balloon is filled. It is also possible to fabricate such a bi-stable member to make a sound indicating to the user that the valve is closed.

Figure 4:
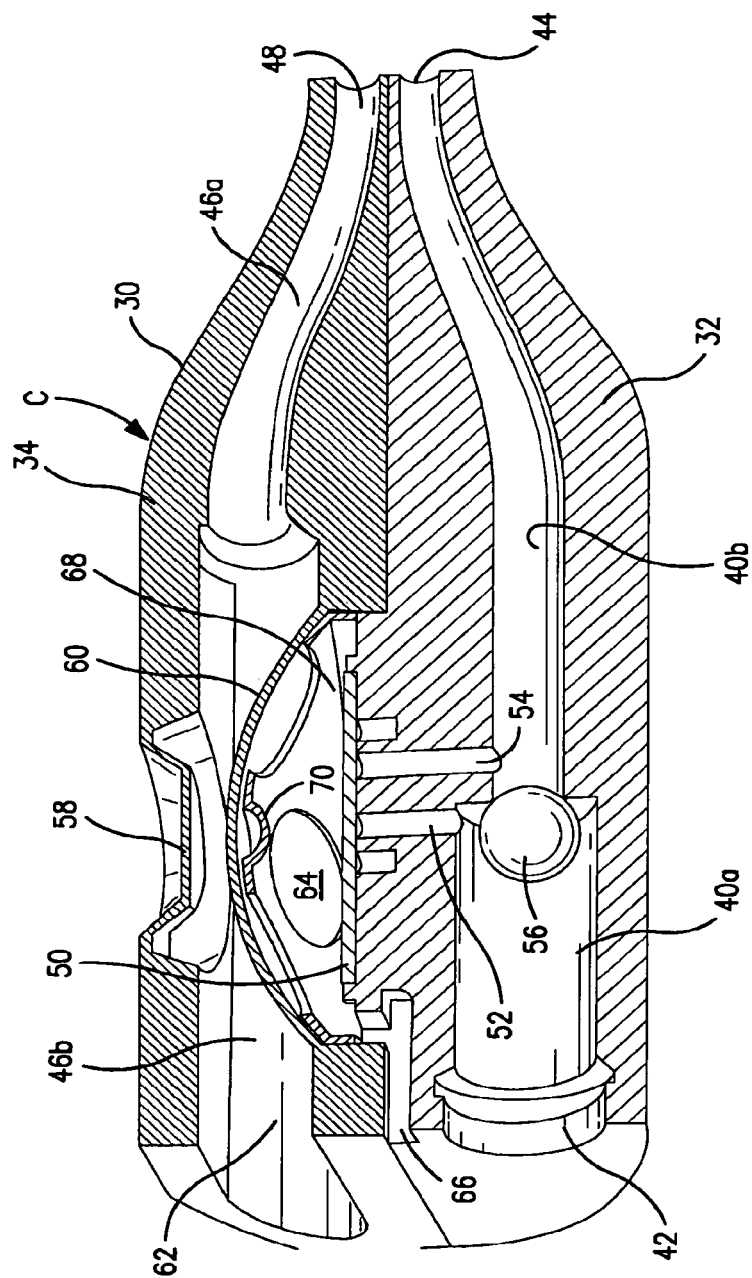
FIG. 4 is a cross-sectional view of a second version of the first preferred embodiment of the present invention.

Member 60 may act in concert with a separate spring element 68, as shown in FIG. 4. FIG. 4 is a cross-sectional view of a second version of the first preferred embodiment of the present invention. This version is the similar to the first version shown in FIG. 3 with the addition of dome-shaped spring element 68 situated under member 60. Element 68 may have several openings therein, as shown. Element 68 urges member 60 towards the position shown in the drawing, remote from membrane 50.

To aid in positive closure of the connection between channels 52 and 54 as member 60 is moved by excess pressure in portion 62 of chamber section 46b to a position against membrane 50, a protrusion 70 may be provided on member 68. Protrusion 70 concentrates the force of member 60 on the membrane 50 at the point of the fluid connection between channels 52 and 54. This force-concentrating function could be performed by a separate component, an element integral with member 60, or a protrusion integral to the spring element, as shown.

High pressure fill is shut off through the mechanical advantage of the large pressure-responsive valve member 60 countering the small open area under membrane 50. The pressure of a syringe fill can reach 1000 mmHg so if the desired shutoff pressure is 35 mmHg, a ratio of 29 or more is required. If the channels 52 and 54 are 2 mm in diameter, for example, the open area under the membrane can be limited to about 18 square mm. This means that the area of the pressure-responsive member should be about 522 square mm. or a diameter of about 13 mm. Smaller ratios would be acceptable as the snap shutoff would be a distinct enough change to indicate that filling should stop. Larger ratios may be desirable if a snap action spring element is employed, as additional force may be needed to change the state of the spring element.

Figure 5:
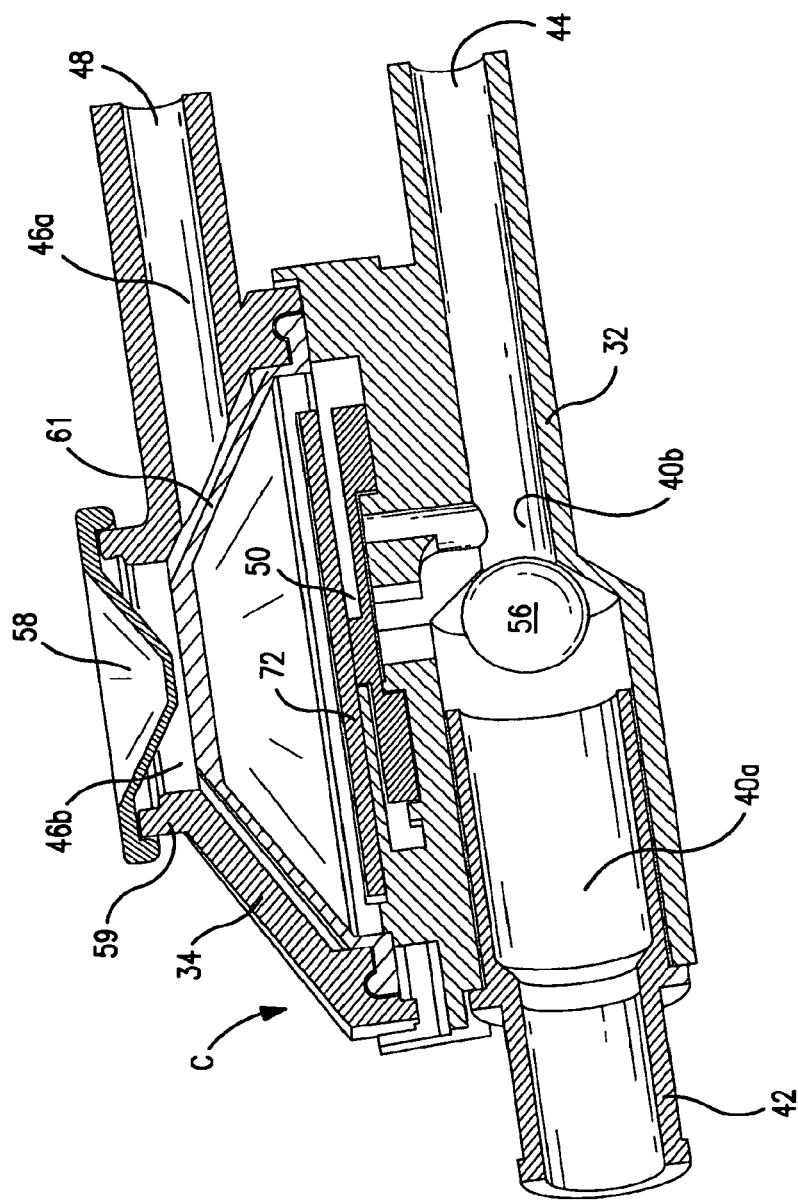
FIG. 5 is a cross-sectional view of a third version of the first preferred embodiment of the present invention.

FIG. 5 illustrates a third version of the first preferred embodiment of the present invention. This version of the apparatus is similar to that of FIG. 3, with the following exceptions. Base 32 and pressure cap 34 each have a somewhat different shape. In particular, cap 34 has a protruding top portion 59 enclosing a "V" shaped pressure indicator 58. The member 60 and separate spring element 68 are replaced by a bi-stable pressure-responsive valve member 61 in the form of a snap dome with a truncated conical shape. Further, in this version, a separate concentrating disc 72 is situated over membrane 50.

Figure 6:
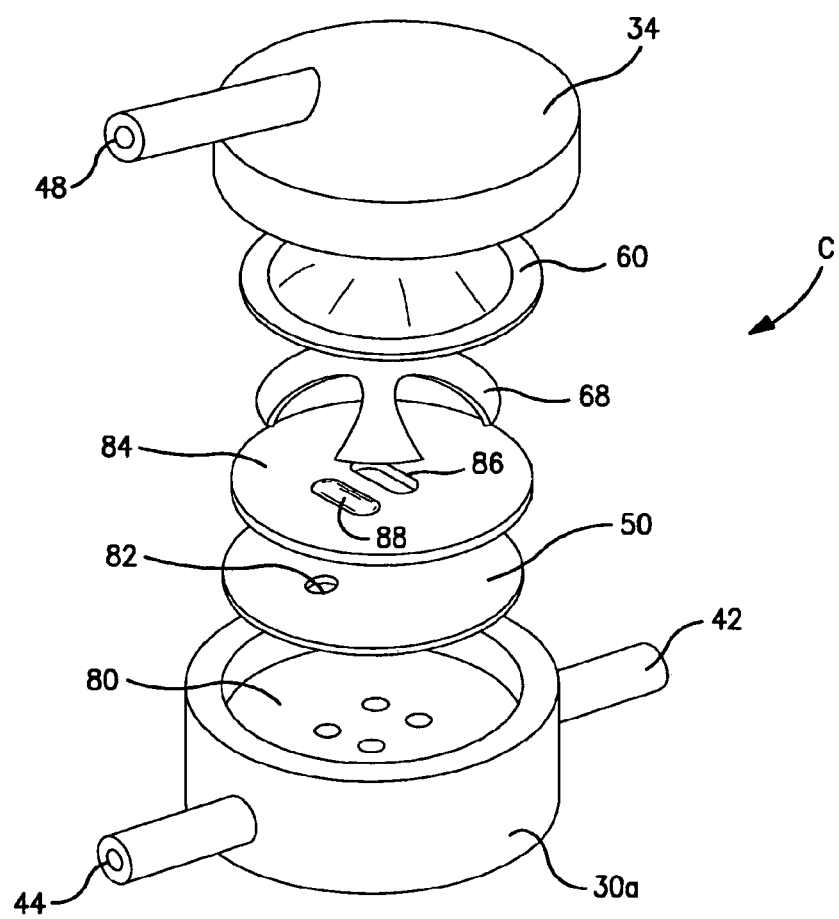
FIG. 6 is an exploded view of a fourth version of the first preferred embodiment of the present invention.
Figure 7:
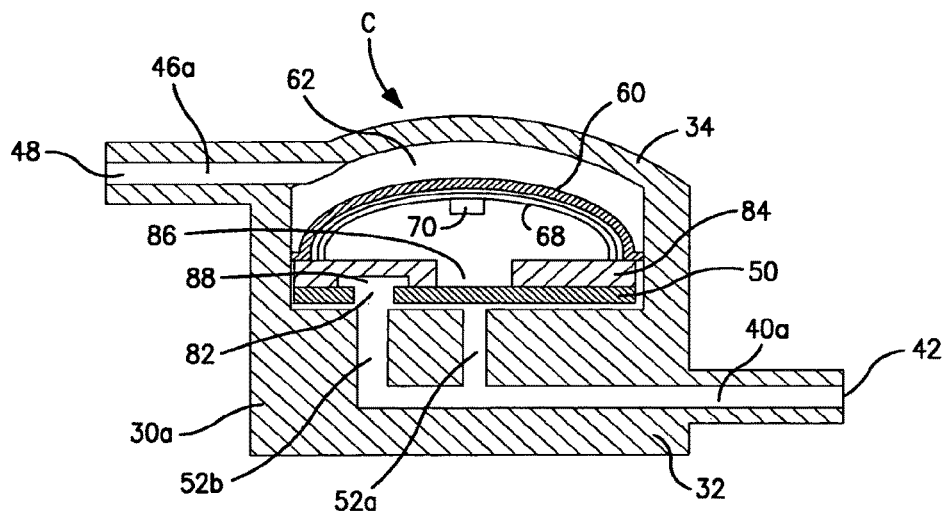
FIG. 7 is a cross-sectional view of the fourth version of the first preferred embodiment of the present invention shown in FIG. 6.

In a fourth version of the first preferred embodiment, shown in FIGS. 6 and 7, two separate flow paths between fluid inlet port 42 and fluid outlet port 44 are created, one for inflation and a second for deflation. Creating separate fluid flow paths eliminates the necessity for having a discrete check valve, such as fill check valve ball 56, with passage section 40b.

In this version, body 30 of the apparatus takes the form of a hollow cylindrical member 30a which has a rigid top surface 80 upon which the flexible element, in the form of membrane 50, is supported. Surface 80 has four openings or ports therein which are situated over the ends of branches of the channels which connect passage sections 40a and 40b, as explained below. In this version, membrane 50 has an opening 82 therein.

A rigid or semi-rigid disc-like retainer 84 is situated over membrane 50 to hold the membrane in place on surface 80. Retainer 84 may be fixed in place in any suitable manner, such as with fasteners, a snap fit, or by bonding it to body 30a. The retainer maintains sealing contact between membrane 50 and surface 80 of body 30a. It includes features that define the areas within which the membrane can flex and allow flow beneath it between desired branches. In particular, retainer 84 has an oval-shaped opening 86 that permits the membrane to flex and allow flow beneath the membrane between branches 52a and 54a and therefore from the inlet 42 to the outlet 44. Furthermore, retainer 84 has an oval shaped relief 88 in its bottom surface that permits the membrane to also flex and allow flow beneath the membrane between branches 54b and 52b and therefore from the outlet 44 to the inlet 42.

Figure 8A:
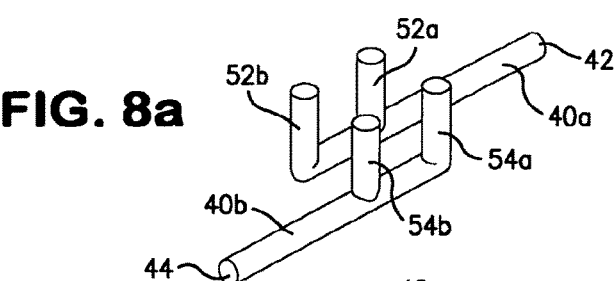
FIGS. 8a-8c are images showing the details of the branches and flow paths of the fourth version of the first preferred embodiment of the present invention, shown in FIG. 7.
Figure 8B:
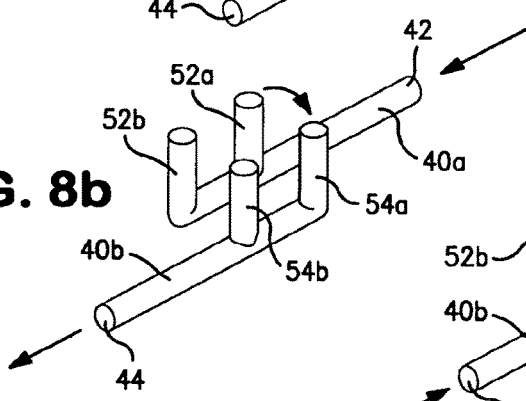
Figure 8C:
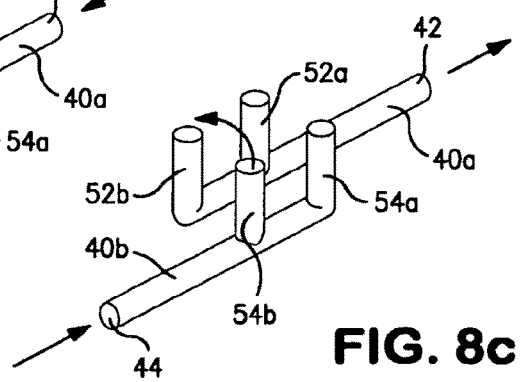

As is best seen from FIGS. 8a-8c, directional control of flow between passage sections 40a and 40b may be achieved by creating two separate flow paths. In order to do that, each of the channels 52 and 54 is separated into two branches 52a, 52b, and 54a, 54b, respectively, as and 52a illustrated in FIG. 8a.

The flow paths under membrane 50, between branches 52a and 54a, and between branches 54a and 54b, are separated from one another, either by retainer 84 or by selective bonding of the membrane to the valve seat surface 80. Opening 82 in membrane 50 is aligned with the end of branch 52b, as shown in FIG. 7. The area above the membrane between branches 54b and 52b is enclosed by relief 88, which prevents fluid that passes through opening 82 from escaping this area.

As is best seen in FIG. 8b, during inflation, fluid can flow from branch 52a to branch 54a, under the portion of membrane 50 aligned with opening 86 in retainer 84. Once the target fluid pressure in the retention balloon is reached, that pressure is present in portion 62 of passage section 46b (see FIG. 7), and causes member 60 to move to its normal position remote from membrane 50 shown in the drawing to a second position, against the urging of spring 68. Movement of member 60 and spring element 68 to that position causes protrusion 70 on spring 68 to move through opening 86 in retainer 84, pressing the aligned portion of membrane 50 toward surface 80, and cutting off the flow from branch 52a to branch 54a, in the same manner as in the aforementioned versions of this preferred embodiment. Alternately the protrusion 70 may be mounted to the top surface of the membrane, concentric with branch 52a.

Once the connection between branches 52a and 54a is obstructed, fluid pressure is directed through branch 52b and opening 82 in membrane 50. That pressurizes the surface of membrane 50 above branch 54b and bounded by relief 88, preventing fluid flow into branch 54b. In this condition, fluid flow out of outlet port 44 is prevented.

When fluid is withdrawn from the balloon, as shown in FIG. 8c, the fluid flows into body 30a from outlet port 44, passes through branch 54b, under membrane 50 into branch 52b, and out of fluid inlet port 42. Under this condition, negative pressure in branch 52a holds the membrane 50 against surface 80, and flow through the body is conducted between branch 54b and branch 52b, and ultimately to passage section 40a and inlet port 42. Under this condition, opening 82 in membrane 50 causes pressure on either side of the membrane to equalize. This prevents the membrane from blocking flow between branches 54b and 52b.

Figure 9:
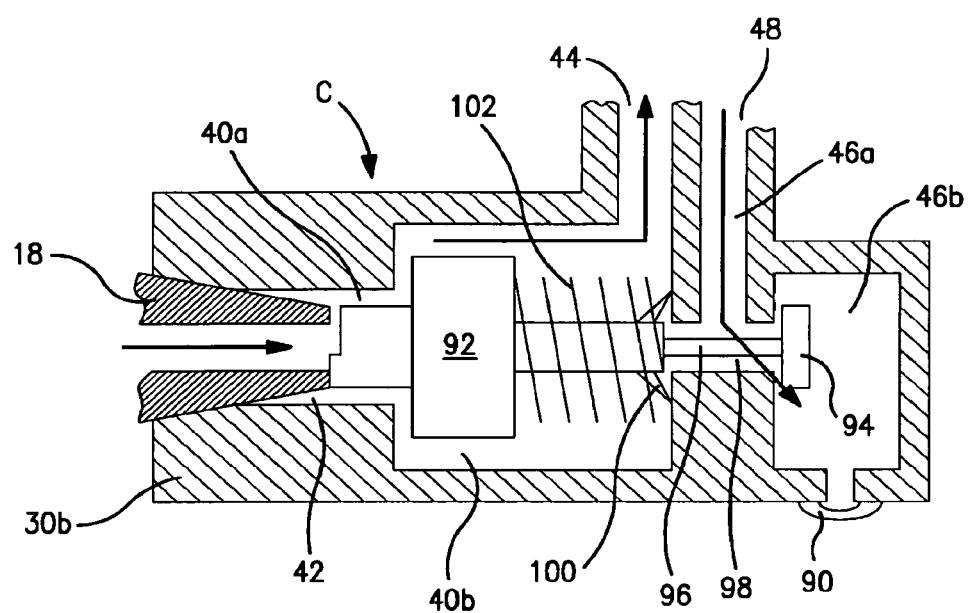
FIG. 9 is a cross-sectional view of a first version of the second preferred embodiment of the present invention.

A first version of a second preferred embodiment of the present invention is illustrated in FIG. 9. In this version, the body 30b of apparatus C has a fluid inlet port 42, a fluid outlet port 44 connected to the fluid inlet of balloon 14 by supply lumen 16, a passage 40 extending from fluid supply port 42 to fluid return port 44, a passage 46 and a return port 48 connecting passage 46 to balloon 14 by return lumen 26, as in the first preferred embodiment, but with a somewhat different layout.

However, in the second preferred embodiment, a pressure relief valve 90 is located in passage section 46b to allow excess fluid to escape from the balloon, but only during inflation of the balloon. Fluid flow from the balloon, through return port 48 and passage section 46a into passage section 46b is prevented by a pair of valves 92 and 94. Valves 92 and 94 are mechanically connected to work together by a connector 96 which extends through a channel 98 between passage 40 and passage 46.

The first valve 92 is situated in passage section 40a between fluid input port 42 and passage section 40b which in turn is connected to fluid outlet port 44. The second valve 94 is situated in channel 98 between passage sections 46a and 46b, thus between return port 48 (and thus the fluid outlet 28 of the balloon) and pressure relief valve 90. Connector 96 causes first valve 92 and second valve 94 to move together from a closed position to an open position (shown in the drawing) in response to the connector associated with the pressurized fluid source, shown in this figure as the tip of syringe 18, being received in fluid inlet port 42 of the body.

Connector 96 may take the form of mechanical means extending between passage section 40b and passage section 46b. A seal 100 is provided for sealing channel 98 such that fluid cannot flow from passage section 40b to passage section 46b.

Spring means 102 associated with valve 92 are provided for urging valve 92 and valve 94 to move from the open position toward the closed position.

Figure 10:
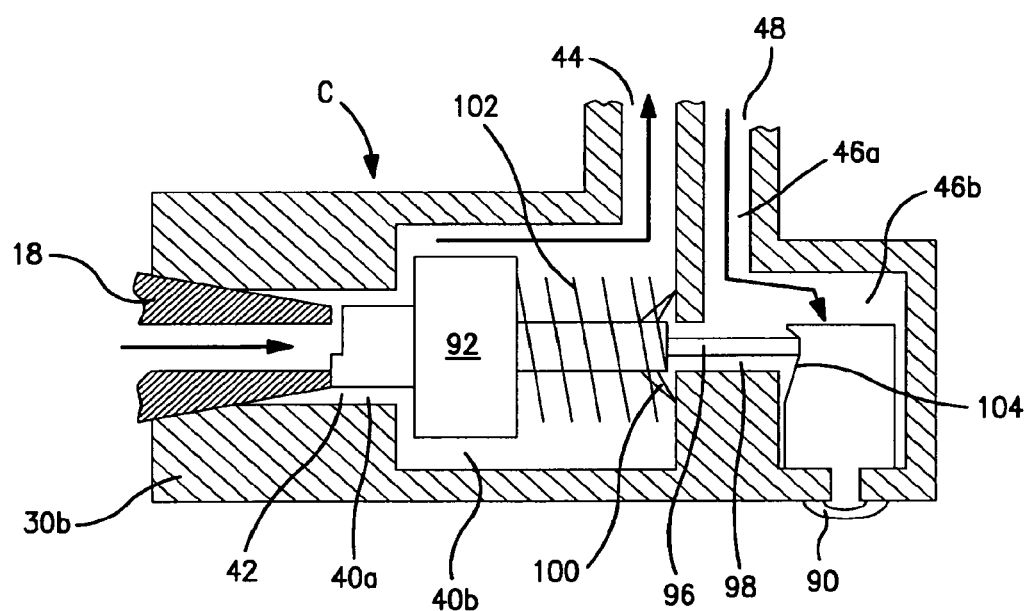
FIG. 10 is a cross-sectional view of a second version of the second preferred embodiment of the present invention.

In a second version of the second preferred embodiment, as illustrated in FIG. 10, valve 94 is replaced by a "duckbill" valve 104 which is opened through lateral deformation of the valve. Otherwise, the structure and operation of the apparatus is essentially the same as in the first version of the second preferred embodiment.

In a third preferred embodiment, the pressure relief valve is eliminated and the valve in chamber section 40a is no longer actuated to open in response to the insertion into fluid inlet port 42 of the connector associated with the pressurized fluid source. However, there is still a spring-loaded valve 110, including a spring 112, associated with fluid inlet port 42 to prevent fluid from escaping through that port when the connector is not present.

Figure 11:
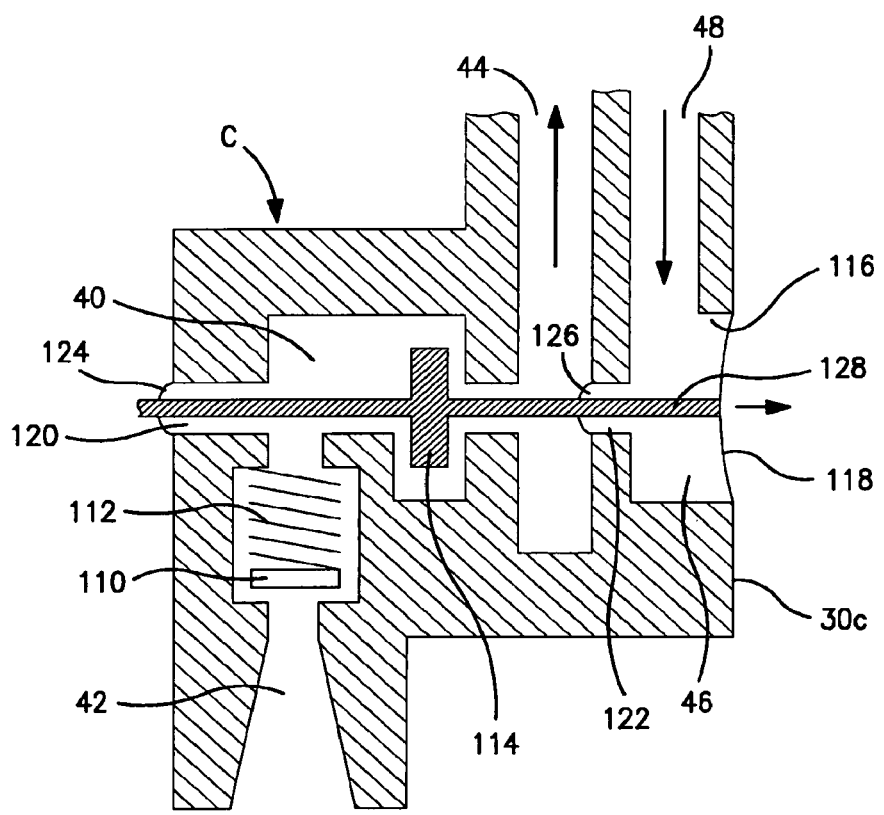
FIG. 11 is a cross-sectional view of a first version of the third preferred embodiment of the present invention.

In the first version of the third preferred embodiment, illustrated in FIG. 11, the fluid flow preventing means includes a normally open valve 114 situated in passage 40 between the fluid input port 42 and the fluid outlet port 44. A portion of the external wall of the body 30c which defines chamber 46, has an opening 116. Situated within opening 116 in the body wall is a flexible means, such as a membrane or a diaphragm 118, which is moveable between the position shown in the drawing, to an extended position in the direction of the arrow. There is also an opening 120 in the wall which defines passage 40 and an opening 122 between passage 40 and passage 46. Openings 120 and 122 are aligned with each other and with opening 116. Flexible seals 124 and 126 are provided to seal openings 120 and 122, respectively.

A connector 128 extends between flexible means 118 and valve 114 such that valve 114 moves with flexible means 118. In the position shown in the drawing, valve 114 opens passage 40 and allows fluid flow between fluid inlet port 42 and fluid outlet port 44 to permit inflation of the balloon. However, when the pressure in the balloon, and hence in chamber 46, exceeds a pre-determined level, flexible means 118 will move to its extended position, in the direction of the arrow. That will cause connector 128 to close valve 114, preventing additional fluid from entering the balloon. Connector 128 can move freely through openings 120 and 122 without any fluid transfer through those openings due to seals 124 and 126.

Figure 12:
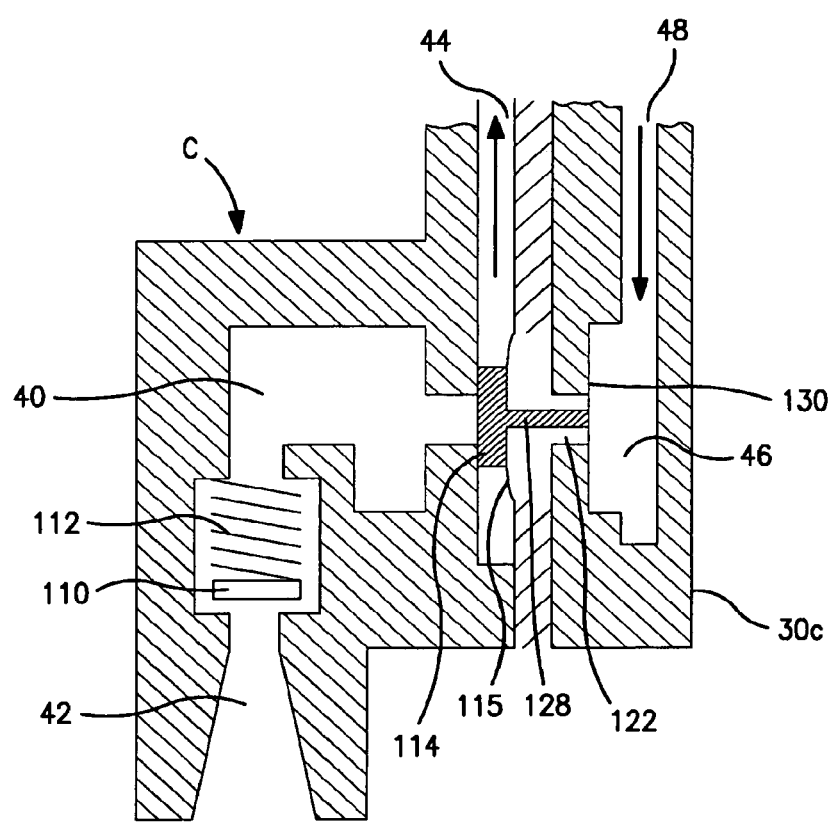
FIG. 12 is a cross-sectional view of a second version of the third preferred embodiment of the present invention.

In a second version of the third preferred embodiment, illustrated in FIG. 12, normally open valve 114 is still present in passage 40 and still permits inflation of the balloon until the predetermined pressure level is reached. However, in this version, valve 114 is mounted on a flexible seal 115, and opening 116 in the external body wall and flexible means 118 are replaced by flexible means 130, situated in chamber 46, which is moveable between its normal open position and a second position, the latter position being illustrated in the drawing. Means 130 in this version may take the form of a diaphragm.

Connecting means 128 connects flexible means 130 and valve 114 for closing valve 114 when flexible means 130 is moved from its normally open position to the second position, shown in the drawing, by the fluid pressure in chamber 46 exceeding the predetermined level.

Figure 13:
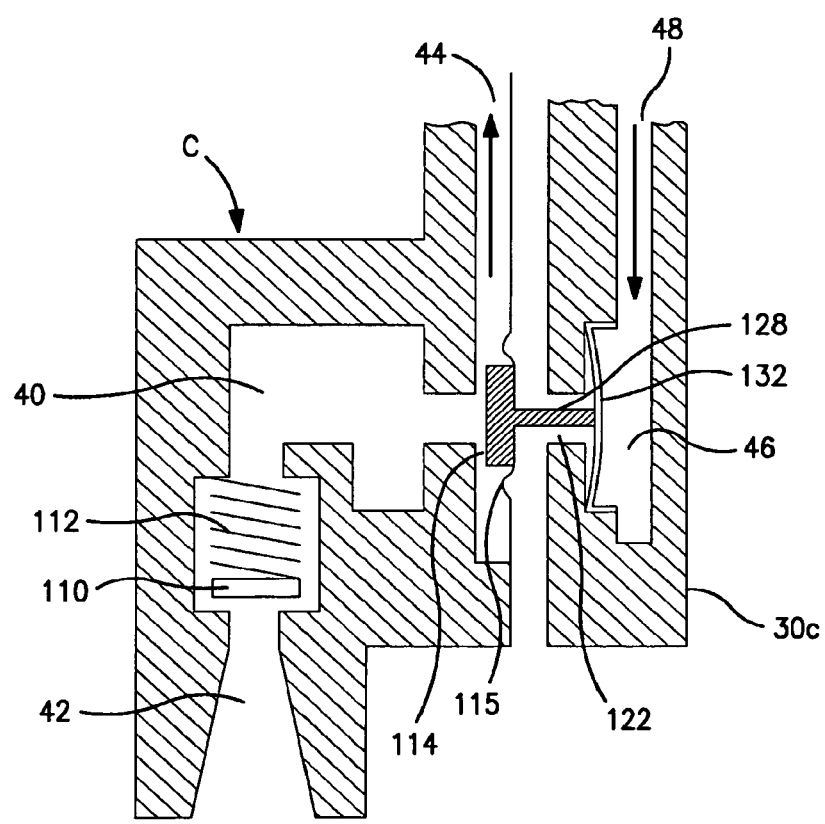
FIG. 13 is a cross-sectional view of a third version of the third preferred embodiment of the present invention.

In a third version of the third preferred embodiment, illustrated in FIG. 13, flexible means 130 takes the form of bi-stable means, preferably a dome-shaped member 132. The dome-shaped member 132 may be formed of rigid or semi-rigid material. In this figure, valve 114 is shown in its normally open position but is moved to a position closing passage 40 in response to the pressure in passage 46 exceeding the predetermined level.

Figure 14:
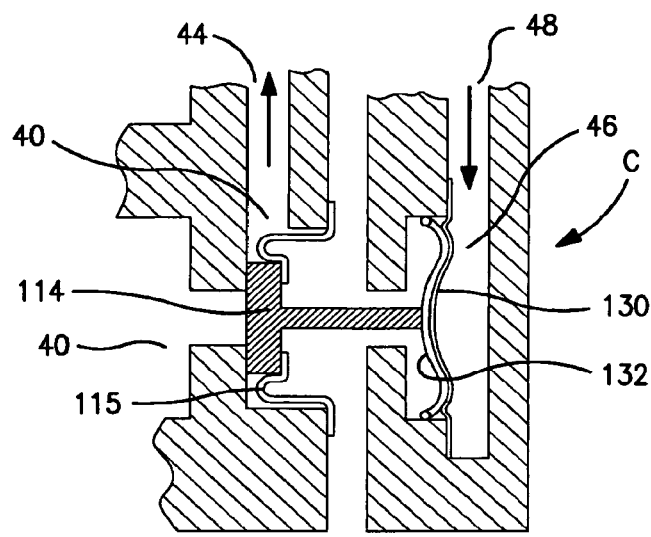
FIG. 14 is a cross-sectional view of a fourth version of the third preferred embodiment of the present invention.

In a fourth version of the third preferred embodiment, illustrated in FIG. 14, flexible means 130 takes the form of a diaphragm 130 which is situated between the dome-shaped member 132 and chamber 46. In this figure, dome shaped member 132 is shown in its flexed position, closing valve 114 such that no additional fluid can be supplied to the balloon though passage 40.

In a fourth preferred embodiment of the present invention, an inflatable return balloon, connected to retention balloon 14 through return lumen 26 and fluid return port 48, is situated within passage 46 of body 30c of the apparatus. The return balloon controls the fluid flow through passage 40. When the return balloon is inflated by a pressure exceeding the pre-determined pressure level in the retention balloon, it prevents further fluid from flowing through passage 40 to balloon 14.

Figure 15:
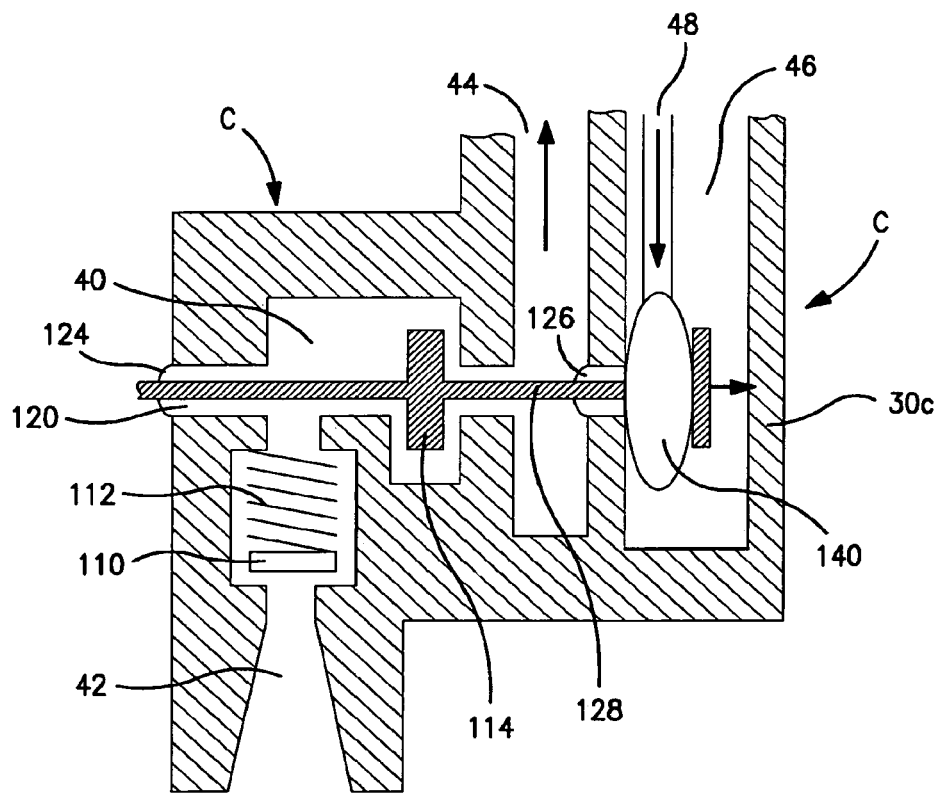
FIG. 15 is a cross-sectional view of a first version of the fourth preferred embodiment of the present invention.

The first version of the fourth preferred embodiment, illustrated in FIG. 15, is similar in structure to the versions of the second preferred embodiment except that return balloon 140 replaces flexible means 118 of FIG. 11, diaphragm 130 of FIG. 112, done-shaped member 132 of FIG. 13 or the dome-shaped/diaphragm combination of FIG. 14, as the means for moving the valve within passage 40.

As shown in FIG. 15, return balloon 140 is connected to return port 48 and hence to balloon 14 through return lumen 26 and balloon return port 28. The fluid flow preventing means includes valve 114 situated in passage 40, between the fluid inlet port 42 and the fluid outlet port 44. Connector 128 extends between the return balloon 140 in passage 46 and valve 114 such that the valve is closed by the inflation of the return balloon 140, when the fluid pressure in the fluid outlet 128 of the retention balloon exceeds the given pressure level.

Preferably, return balloon 140 has a toroidal shape and defines a central opening. Connector 128 extends though the central opening in the return balloon.

Figure 16:
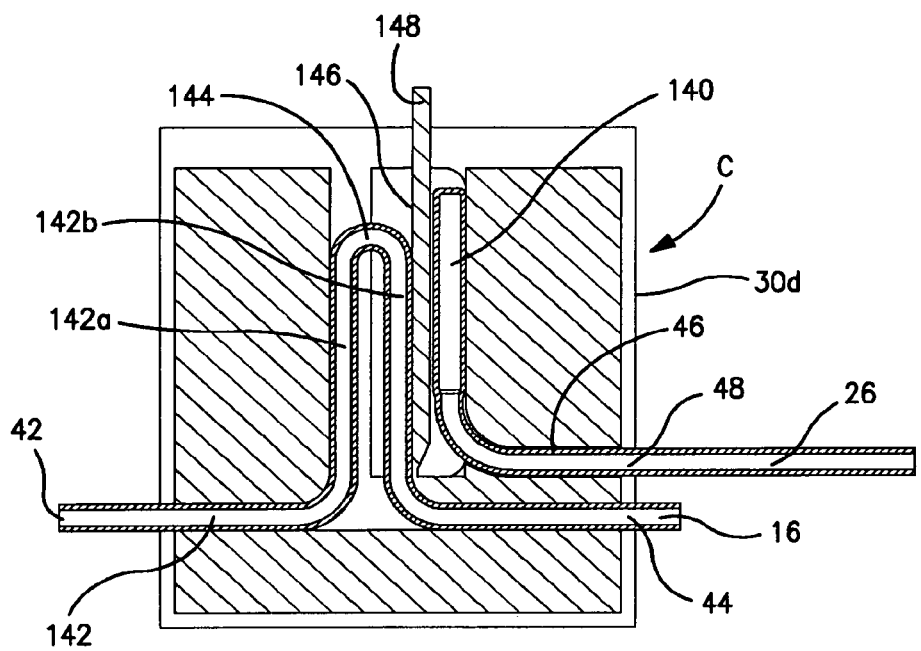
FIG. 16 is a cross-sectional view of a second version of the fourth preferred embodiment of the present invention.
Figure 17:
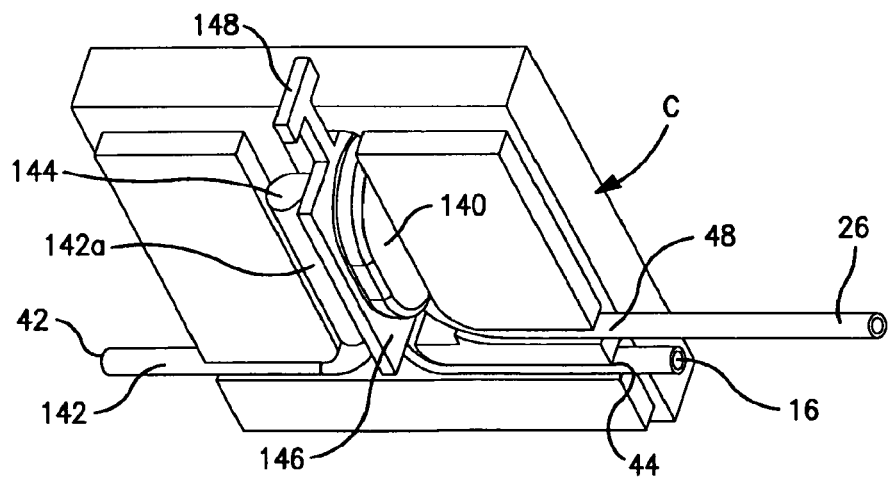
FIG. 17 is a perspective view of the second version of the fourth preferred embodiment of the present invention.

A second version of the fourth preferred embodiment is illustrated in FIG. 16, which is a cross-sectional view of a different configuration apparatus body 30d and FIG. 17 which shows the apparatus in perspective view. In this version, passage 40 takes the form of a flexible tube 142. The return balloon 140 in passage 46 closes flexible tube 142 to cut off fluid flow to retention balloon 14 when return balloon 140 is inflated by pressurized fluid in the fluid outlet 28 of the retention balloon exceeding the predetermined pressure level.

Preferably, flexible tube 142 has first and second substantially parallel sections 142a and 142b. The parallel sections 142a and 142b are connected by a "U" shaped section 144. The return balloon 140, when inflated with fluid beyond the predetermined pressure level, presses on parallel sections 142a, 142b of tube 140 to close the tube and prevent further fluid flow to the retention balloon.

A pressure plate 146 may be interposed between the return balloon 140 and flexible tube 142, adjacent parallel sections 142a and 142b. A pressure indicator 148 associated with pressure plate 146 may be used as a visual indicator of the fluid pressure in the retention balloon.

Figure 18:
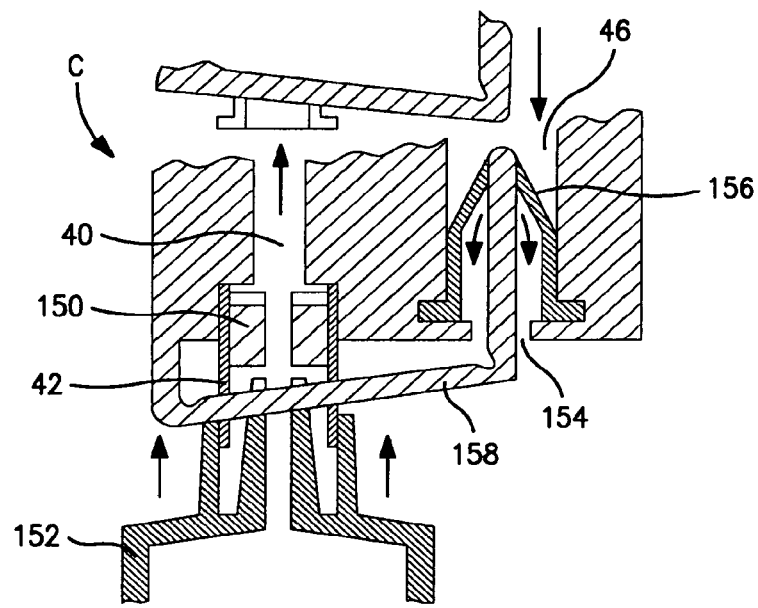
FIG. 18 is a cross-sectional view of a first version the fifth preferred embodiment of the present invention, showing same during and after inflation of the balloon.
Figure 19:
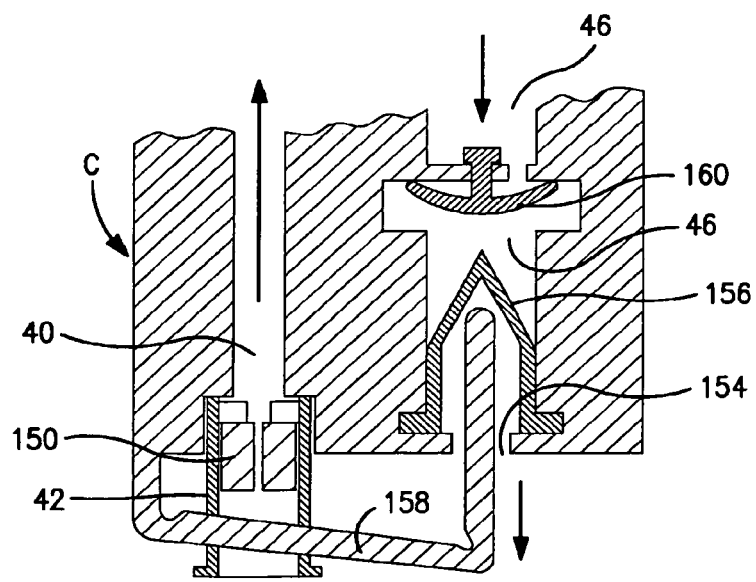
FIG. 19 is a cross-sectional view of a second version of the fifth preferred embodiment of the present invention.

The fifth preferred embodiment of the present invention is illustrated in FIGS. 18 and 19. In this embodiment, a valve 150 is associated with fluid inlet port 42. Valve 150 is normally in a closed position. The valve is moveable to an open position when a Luer-type connector 152 associated with a pressurized fluid source is received in the fluid inlet port 42 of the body.

In the first version of the fifth preferred embodiment, illustrated in FIG. 18, the over inflation preventing means includes a port 154 in passage 46. A duckbill check valve 156 is associated with port 154. A pivot arm 158 is actuated by the Luer-type connector 152 associated with the pressurized fluid source being received in the fluid inlet port 42 of the body to open the duckbill check valve 156. Opening the duckbill check valve 156 allows excess fluid to escape passage 46 and hence prevent over inflation of the retention balloon.

FIG. 19 illustrates a second version of the fifth preferred embodiment of the present invention. This version is similar to the version illustrated in FIG. 18 except that an umbrella pressure relief valve 160 is situated in passage 46 between the fluid outlet of the retention balloon and duckbill check valve 156. The flexible structure of umbrella valve 160 urges the umbrella valve toward the closed position. However, when the pressure in the retention balloon exceeds the predetermined pressure level, umbrella valve 160 will open allowing excess fluid to pass and be expelled during inflation, when the Luer-type connector is received in fluid inlet port 42, opening the duckbill valve 156.

In all of the above preferred embodiments, the connector associated with the pressurized fluid source may take the form of a portion of a syringe or a Luer-type connector. Further, means for visually indicating when the pressure of the fluid in the retention balloon exceeds the pre-determined pressure level may be employed. For example, as seen in FIGS. 3, 4 and 5, the pressure indicating means may take the form of a means associated with the wall of passage 46 which is movable between a normal position and an extended position. The pressure indicating means moves from its normal position to its extended position in response to the fluid pressure in the second passage exceeding the predetermined level.

In the volume monitoring approach to the over inflation problem, three different preferred embodiments are described, as follows.

The sixth preferred embodiment of the present invention is illustrated in FIGS. 20 through 25. FIGS. 20 and 21 show the arrangement of the components of this embodiment, before and after balloon inflation, respectively. A paddle wheel is used to monitor the volume of fluid provided to and removed from retention balloon 14. Paddle wheel 170 is connected to a manually actuated syringe 18. Associated with paddle wheel 170 is a pressure accumulator 172. The paddle wheel 172 rotation operates a valve 174 situated between the paddle wheel and supply lumen 16. Valve 174 is closed to prevent additional fluid from being provided to the retention balloon when the volume of fluid in the balloon exceeds a predetermined level.

All fluid flow into and out of the retention balloon is forced to pass through paddle wheel 170. The paddle wheel 170 is rotated by the fluid flow. If the fluid is incompressible, the paddle wheel rotation 172 will accurately monitor the amount of fluid passing through the paddle wheel. When the desired amount of fluid is in the retention balloon, the accumulated rotation of the paddle wheel causes valve 174 to close, preventing additional fluid from flowing into the retention balloon and hence over inflation of the retention balloon.

FIG. 20 shows that as force is applied to the plunger of syringe 18, fluid flows through the paddle wheel housing 180, rotating the paddle wheel 170 therein, and through valve 174 which is open, up the supply lumen 16 and into retention balloon 14. As shown in FIG. 21, as additional force is applied to the plunger of syringe 18, the paddle wheel continues to rotate until the predetermined volume of fluid has been provided to the retention balloon. At that point, the accumulated rotation of the paddle wheel result in valve 174 being closed, preventing further fluid from entering the retention balloon.

FIG. 22 is a perspective view showing the components of this embodiment in greater detail. FIG. 23 is an exploded view of the components. FIGS. 24 and 25 show in detail the mechanical connection between the paddle wheel the valve.

The paddle wheel 170 is situated in a housing 180. Housing 180 has an inlet port 182 connected to receive fluid from the syringe and an outlet port 184 connected to the retention balloon through supply lumen 16 and valve 174. In this embodiment valve 174 takes the form of a sleeve valve. Valve 174 has a cylindrical housing 183 and an internal valve body 185 which rotates within housing 183.

A cam follower member 186 is fixed to the end of the rotatable valve body 185 such that rotation of the cam follower member causes the valve body to rotate within the valve housing. The valve body 185 is hollow and has aligned fluid ports 188 on either side, only one of which is visible in FIG. 23. When the valve body is in the position shown in FIG. 23, the valve is closed and no fluid can flow from the syringe to the retention balloon. When the valve body is rotated by the cam follower member 90 degrees, ports 188 of valve body align with port 184 of valve housing 183 and supply lumen 16 such that fluid can flow from the syringe to the retention balloon.

Valve cam 190 is situated on the end of housing 180. It has a cylindrical configuration with an open end which faces the paddle wheel within housing 180. As seen in the cut-away portion of the valve cam in FIG. 23, the interior surface of the side wall of valve cam 190 has a circumferential channel 190 with an L-shaped end, best seen in FIGS. 24 and 25.

Valve cam 190 is rotated by cam drive gears 192 between a valve closed position shown in FIG. 24 and a valve open position shown in FIG. 25. The valve cam is normally in the valve open position as fluid is provided from the syringe to the retention balloon and paddle wheel 170 is rotated. The diaphragm 194 of accumulator 172 allows a limited volume of fluid to collect in the accumulator. The fluid stored in the accumulator allows enough fluid volume to be withdrawn to permit the paddle wheel to rotate in a reversed direction sufficiently for the valve to reopen.

FIGS. 24 and 25 show the "L" shaped end of channel 196. When valve cam 190 moves from the valve open position of FIG. 25 to the valve closed position of FIG. 24, cam follower member 186 is rotated one quarter turn in the counterclockwise direction. That causes valve body 185 to rotate to close valve 174 and prevent additional fluid from entering the balloon. When the plunger of the syringe is withdrawn from the syringe body to deflate the retention balloon, the vacuum caused by the withdrawal of the plunger causes the paddle wheel 170 to rotate in the opposite direction, which in turn causes the valve cam 190 to return to its valve open position. That opens valve 174 and allows the fluid in the retention balloon to flow back into the syringe.

Figure 26:
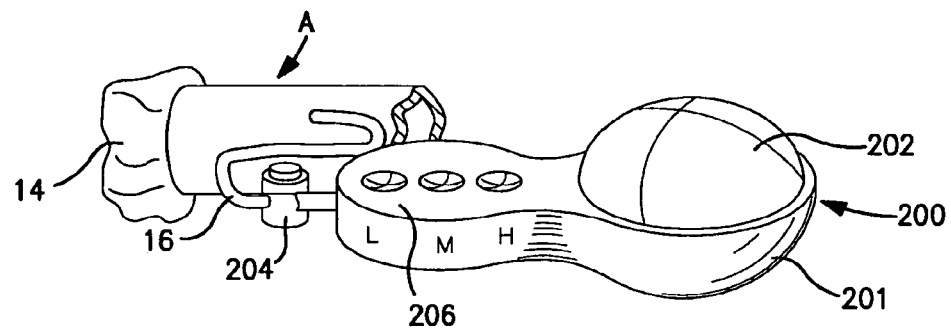
FIG. 26 is a perspective view of the seventh preferred embodiment of the present invention, showing the collapsible reservoir prior to inflation.
Figure 27:
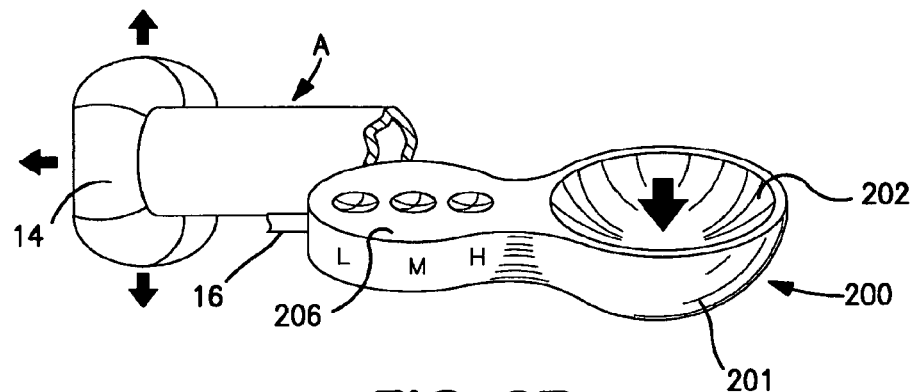
FIG. 27 is a perspective view of the seventh preferred embodiment of the present invention, showing the collapsible reservoir after the balloon is inflated.
Figure 28:
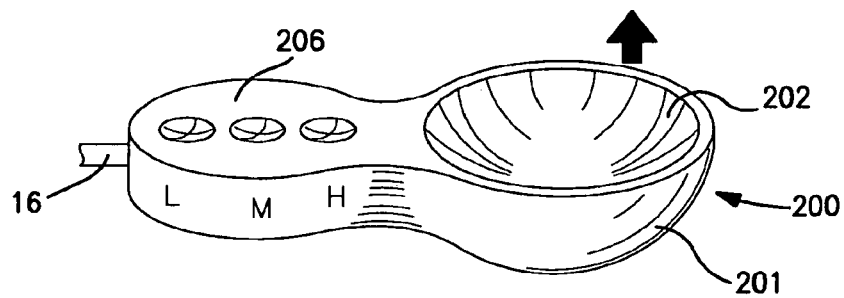
FIG. 28 is a perspective view of the seventh preferred embodiment of the present invention, showing the collapsible reservoir during deflation of the balloon.

A seventh preferred embodiment of the present invention is illustrated in FIGS. 26, 27 and 28 which show the apparatus prior to balloon inflation, after balloon inflation and during balloon deflation, respectively. In this preferred embodiment, the fluid system is closed, meaning that a fixed amount of fluid remains in the system but is transferred between a collapsible reservoir and the retention balloon.

As seen in these figures, this embodiment of the apparatus includes a fluid reservoir 200 with a rigid bottom housing 201 having one section with a collapsible top 202. Applying pressure to top 202 reduces the interior volume of the reservoir forcing fluid from the housing into retention balloon 14 through supply lumen 16. Situated within the other section of housing 201, between the section with collapsible top 202 and the connection to the supply lumen, is a set of three pressure indicators 206 which indicate when the pressure in the retention balloon is low (L), medium (M) or high (H). A manually actuated valve 204 is located between reservoir 200 and the supply lumen.

FIG. 26 shows the apparatus prior to inflation. In that state, collapsible top 202 has a done-like configuration.

The balloon is inflated by applying pressure to the flexible top 202 of reservoir 200 such that fluid is force out of reservoir 200 and into the retention balloon through pressure indicator 206, open valve 204 and lumen 16. As seen in FIG. 27, when pressure is applied to top 202, it collapses into the housing to force the fluid into the retention balloon. When the pressure indicator 206 indicates that the pressure in the balloon has reached the desired level, because a sufficient volume of fluid has been provided to fully inflate the balloon, the operator closes valve 204.

As seen in FIG. 28, during deflation, valve 204 is opened by the operator and the force applied to the top 202 of the reservoir is released such that top 202 can return to its normal dome-like shape. That causes fluid from the balloon to leave the balloon and flow back into the reservoir, deflating the balloon.

Figure 29:
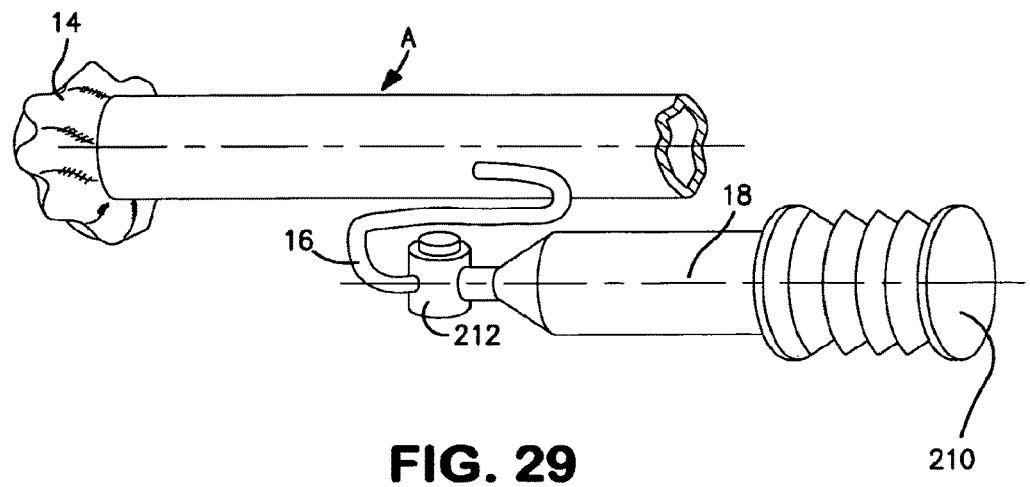
FIG. 29 is a perspective view of the eighth preferred embodiment of the present invention, showing a sealed syringe fluid source prior to inflation.
Figure 30:
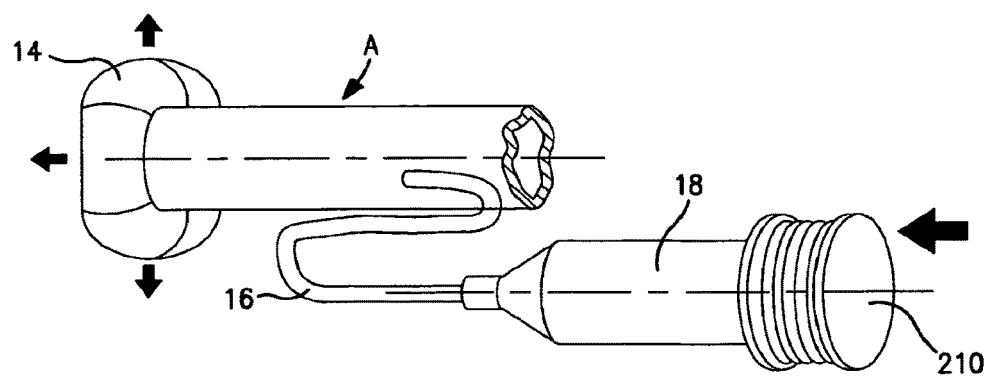
FIG. 30 is a perspective view of the eighth preferred embodiment of the present invention, showing the sealed syringe fluid source during balloon inflation.

An eighth preferred embodiment of the present invention is illustrated in FIGS. 29 and 30. This embodiment also has a closed volume system with a fixed amount of fluid and utilizes a variable volume reservoir to provide fluid to and remove fluid from the retention balloon. In this embodiment, the variable volume reservoir takes the form of a syringe 18 with an associated bellows-like portion 210. A manually actuated valve 212 is situated between syringe 18 and supply lumen 16.

FIG. 29 shows the apparatus prior to balloon inflation. In this state, bellows-like portion 210 is in its most extended position such that the capacity of the syringe is at its highest level. During the inflation process, as illustrated in FIG. 30, force is applied to bellows-like portion 210 such that it collapses, reducing the internal volume of the reservoir and causing fluid to move from the syringe, through valve 212 and lumen 16 to the balloon. When the balloon is fully inflated, valve 212 is closed by the operator such that the fluid is retained in the balloon. During deflation, valve 212 is opened and the fluid from the balloon flows back into the syringe, causing bellows-like portion 210 to expand as the balloon deflates.

A pressure gauge, or other means of indicating the pressure in the system, not shown, may be used to alert the user when the balloon is inflated to a desired pressure and the valve should be closed. The total volume available to fill the balloon is limited thus preventing gross overfill.

It will now be appreciated that the present invention relates to a catheter retention balloon fill line shut off apparatus that utilizes the pressure in a fluid return connection to the balloon, separate from the fluid supply connection to close a valve associated with the fill line to stop the inflow of fluid. The fill line shut off apparatus is connected to or incorporated in the fill port of the catheter.

In one preferred embodiment, pressure in the return line expands or inverts a flexible element displacing a valve and stopping flow into the balloon. The flexible element may be a membrane, diaphragm, balloon or tube. A snap action spring may be used for closing the overfill preventer valve when the pressure in the balloon reaches a predetermined valve and the pressure in the return valve actuates the snap action spring.

The flexible member is secured to a base to create a path to carry fluid from the supply side port to the outlet side of the valve. A pressure-responsive deforming member presses on the membrane to seal the fluid flow path. The deformable member has an area significantly larger than the flow area under the membrane to permit the lower pressure of the retention balloon to stop the higher pressure flow.

Preferably, the pressure-responsive member may take the form of a dome. The member deforms suddenly when a predetermined pressure is reached. The deformable structure incorporates or is made as a snap dome.

The apparatus body is formed of two molded structures that do not have flow passing between them except through the catheter balloon. An integrated indicator that signals prior to or simultaneous with the valve closing off may be provided. The indicator is capable of expanding to indicate the pressure in the return line.

A check valve controls a secondary flow path for removing fluid from the balloon. The check valve element is a ball, flap, duck bill, or umbrella valve. In another embodiment, the check valve element consists of two or more additional ports in conjunction with the flexible membrane.

The deformable structures are molded silicone rubber, polyurethane or other thermoplastic elastomer.

In another preferred embodiment, a pressure relief valve drains inside or outside of the catheter. The pressure relief valve may be located inside or outside of the patient when the distal end of the catheter is retained within the patient's rectum. The fluid is only accessible to the pressure relief valve during inflation, when the connector associated with the pressurized fluid source is connected to the catheter.

In another embodiment, a Luer or other connector actuated double valve is utilized to regulate fluid access to the relief valve. The double valve includes a first valve with a valve system. The valve stem extends into a chamber to open a second valve. The second valve is a duckbill valve. The valve stem distorts the duckbill valve to open it. The second valve includes a valve cap and valve seat. The valve cap is held against the valve seat unless the second valve is actuated. The first and second valves are integrated into a single part.

In another embodiment, the overfill protector includes two chambers, a fill chamber and a return chamber. A compliant sealing element is mounted on said valve stem. The compliant sealing element seals a stem opening between the two chambers when the valves are actuated.

In another embodiment, a membrane is associated with the valve stem. The return line fluid pressure expands or inverts the membrane so as to pull the valve stem and close the fill line valve stopping fluid flow into the balloon. A flexible membrane seal is between the fill line and return line. The valve stem extends outside the opposite side of the fill chamber with a flexible membrane seal so as to balance the fill chamber pressure of the valve stem. The seal between the fill line and the return line is a sliding seal between the housing and valve stem.

In another embodiment, the balloon is inflated by the return line causing a valve stem to close a valve on the fill line. The balloon is annular or nearly annular and the valve stem passes through the opening in the balloon.

In another embodiment, flexible tubing capable of being crimped is part of the fill line. A return balloon inflated by the return line crimps the tubing, stopping fluid flow into the retention balloon. A stiff element may be situated between the crimpable tubing and the return balloon. The stiff element concentrates the force from the return balloon on the tubing. The stiff element may also act as a pressure indicator.

While only a limited number of preferred embodiments of the present invention have been disclosed for purposes of illustration, it is obvious that many modifications and variations could be made thereto. It is intended to cover all of those modifications and variations which fall within the scope of the present invention, as defined by the following claims.

We claim:

1. An apparatus for limiting fluid pressure in a medical catheter retention balloon designed for use with a source of pressurized fluid having a connector associated therewith, wherein a catheter comprising the medical catheter retention balloon has a supply fluid path from the apparatus for filling the medical catheter retention balloon and a separate return fluid path communicating with the medical catheter retention balloon connected to the apparatus, the apparatus comprising:
   a body with a fluid inlet port for receiving the connector associated with the pressurized fluid source, and a fluid outlet port for fluid connection to the supply fluid path;
   a first passage connecting said fluid inlet port and the fluid outlet port of said body;
   a second passage for fluid connection to said return fluid path, wherein the first passage and the second passage are fluidically separated in the apparatus by a fluid flow preventer movable between a first position and a second position, the fluid flow preventer preventing fluid flow through said first passage in the second position when the fluid pressure in said second passage exceeds a predetermined level; and wherein the first passage and the second passage are fluidically separated by the fluid flow preventer when the fluid flow preventer is in the first position and when the fluid flow preventer is in the second position.

2. The apparatus of claim 1 further comprising a pressure relief valve located in said second passage, and wherein said fluid flow preventer comprises a first valve and a second valve, said first valve being situated in said first passage between said fluid inlet port and said fluid outlet port, said second valve being situated in said second passage between a fluid outlet of said medical catheter retention balloon and said pressure relief valve, and means for connecting said first valve and said second valve to move together from a closed position to an open position in response to the connector associated with the pressurized fluid source being received in said fluid inlet port of said body.

3. The apparatus of claim 2 further comprising means for urging said first valve and said second valve to move from said open position to said closed position.

4. The apparatus of claim 2 further comprising mechanical means for connecting said first valve and said second valve, said mechanical means extending between said first passage and said second passage, and further comprising means for sealing said first passage from said second passage.

5. The apparatus of claim 2 wherein said second valve comprises a duckbill valve.

6. The apparatus of claim 1 wherein said fluid flow preventer comprises a normally open valve situated in said first passage between said fluid inlet port and said fluid outlet port, flexible means situated in said second passage, and means for connecting said flexible means and said normally open valve for closing said normally open valve when the fluid pressure in said second passage exceeds the predetermined level.

7. The apparatus of claim 6 further comprising means for sealing said first passage from said second passage.

8. The apparatus of claim 6 wherein said second passage comprises a wall with an opening and wherein said flexible means is associated with said wall opening.

9. The apparatus of claim 1 wherein said fluid flow preventer comprises a normally open valve situated in said first passage between said fluid inlet port and said fluid outlet port, means situated in said second passage moveable between a normal position and a second position, and means for connecting said moveable means and said normally open valve for closing said normally open valve when said moveable means is moved to said second position of said moveable means by the fluid pressure in said second passage exceeding said predetermined level.

10. The apparatus of claim 9 wherein said moveable means comprises bistable means.

11. The apparatus of claim 10 wherein said bistable means comprises a dome-shaped member.

12. The apparatus of claim 11 wherein said dome-shaped member is formed of rigid or semi-rigid material.

13. The apparatus of claim 11 wherein said moveable means further comprises a diaphragm situated proximate said dome-shaped member.

14. The apparatus of claim 9 further comprising means for sealing said first passage from said second passage.

15. The apparatus of claim 1 wherein said fluid flow preventer comprises a valve in said first passage between said fluid inlet port and said fluid outlet port, an inflatable balloon situated in said second passage and connected to a fluid outlet of said medical catheter retention balloon, and means for connecting said inflatable balloon in said second passage and said valve such that said valve is closed by inflation of said inflatable balloon in said second passage when the fluid pressure in said fluid outlet of said medical catheter retention balloon exceeds the predetermined level.

16. The apparatus of claim 15 wherein said inflatable balloon in said second passage defines a central opening through which said connecting means extends.

17. The apparatus of claim 1 wherein said first passage comprises a flexible tube and wherein said fluid flow preventer comprises a balloon in said second passage connected to a fluid outlet of the medical catheter retention balloon, said balloon in said second passage closing said flexible tube when inflated by pressurized fluid in the fluid outlet of the medical catheter retention balloon exceeding said predetermined level.

18. The apparatus of claim 17 wherein said flexible tube comprises first and second substantially parallel sections connected by a "U" shaped section.

19. The apparatus of claim 17 further comprising a pressure plate interposed between said balloon in said second passage and said flexible tube.

20. The apparatus of claim 19 further comprising a pressure indicator associated with said pressure plate.

21. The apparatus of claim 1 further comprising a valve associated with said fluid inlet port of said body, said valve being normally in a closed position and moveable to an open position when the connector associated with said pressurized fluid source is received in said fluid inlet port of said body.

22. The apparatus of claim 21 wherein said fluid flow preventer comprises a port in said second passage, a duckbill check valve associated with said port and a means actuated by the connector associated with said pressurized fluid source being received in said fluid inlet port of said body to open said duckbill check valve.

23. The apparatus of claim 22 further comprising an umbrella pressure relief valve situated in said second passage between a fluid outlet of said medical catheter retention balloon and said duckbill check valve.

24. The apparatus of claim 23 further comprising means for urging said umbrella pressure relief valve toward a closed position.

25. The apparatus of claim 21 wherein the connector associated with the pressurized fluid source comprises a part of a syringe.

26. The apparatus of claim 21 wherein the connector associated with the pressurized fluid source comprises a Luer-type connector.

27. The apparatus of claim 1 wherein said pressurized fluid source comprises a syringe.

28. The apparatus of claim 1 wherein the connector associated with the pressurized fluid source comprises a Luer-type connector.

29. The apparatus of claim 1 further comprising pressure indicating means for visually indicating when the fluid pressure in a fluid outlet of said medical catheter retention balloon exceeds said predetermined level.

30. The apparatus of claim 29 wherein said second passage has a wall and wherein said pressure indicating means comprises means associated with said wall movable between a normal position and an extended position, wherein said pressure indicating means moves from said normal position to said extended position in response to the fluid pressure in said second passage exceeding the predetermined level.

* * * * *